(12) United States Patent
Soon-Shiong et al.

(10) Patent No.: US 11,278,606 B2
(45) Date of Patent: *Mar. 22, 2022

(54) METHODS OF PREPARING CANCER TREATMENTS AND METHODS OF TREATING CANCER

(71) Applicant: Nant Holdings IP, LLC, Culver City, CA (US)

(72) Inventors: Patrick Soon-Shiong, Los Angeles, CA (US); Chihwei Chang, Los Angeles, CA (US)

(73) Assignees: NANT HOLDINGSIP, LLC, Culver City, CA (US); NANOCAV, LLC, Culver City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/115,420

(22) Filed: Dec. 8, 2020

(65) Prior Publication Data

US 2021/0177950 A1 Jun. 17, 2021

Related U.S. Application Data

(60) Provisional application No. 62/947,819, filed on Dec. 13, 2019.

(51) Int. Cl.
| | |
|---|---|
| *A61K 39/00* | (2006.01) |
| *A61K 48/00* | (2006.01) |
| *C12N 5/0783* | (2010.01) |
| *C12N 15/11* | (2006.01) |
| *C12N 15/63* | (2006.01) |
| *B01L 3/00* | (2006.01) |
| *C07K 16/28* | (2006.01) |
| *C12M 1/42* | (2006.01) |

(52) U.S. Cl.
CPC .... *A61K 39/0011* (2013.01); *B01L 3/502715* (2013.01); *C07K 16/2818* (2013.01); *C12M 35/02* (2013.01); *A61K 2039/5154* (2013.01); *B01L 2300/0645* (2013.01)

(58) Field of Classification Search
None
See application file for complete search history.

(56) References Cited

U.S. PATENT DOCUMENTS

| | | |
|---|---|---|
| 2004/0241147 A1 | 12/2004 | Nardin et al. |
| 2017/0037357 A1 | 2/2017 | Cattaruzzi et al. |
| 2020/0340014 A1 | 10/2020 | Chang |

FOREIGN PATENT DOCUMENTS

| | | |
|---|---|---|
| WO | 2020014264 A1 | 1/2020 |

OTHER PUBLICATIONS

Sultan et al, The route of administration dictates the immunogenicity of peptidebased cancer vaccines in mice, Cancer Immunology, Immunotherapy (2019) 68:455-466.*
Hollinsworth and Jansen, Turning the corner on therapeutic cancer vaccines, npj Vaccines (2019) 4:7, pp. 1-10.*
Saxena and Bhardwaj, Re-emergence of Dendritic Cell Vaccines for Cancer Treatment, Trends Cancer. Feb. 2018 ; 4(2): 119-137.*
Van Gulijk et al, Combination Strategies to Optimize Efficacy of Dendritic Cell-Based Immunotherapy, Front. Immunol., Dec. 5, 2018, pp. 1-14.*
Ziv et al, Micro-electroporation of mesenchymal stem cells with alternating electrical current pulses, Biomedical devices, 2008, pp. 95-101.*
Bol et al, The clinical application of cancer immunotherapy based on naturally circulating dendritic cells, Bol et al. Journal for ImmunoTherapy of Cancer (2019) pp. 1-13.*
Van Nuffel et al, Loading of dendritic cells for immunotherapy, ISBT Science Series (2013) 8, 161-164.*
Kamigaki et al, Immunotherapy of Autologous Tumor Lysate-loaded Dendritic Cell Vaccines by a Closed-flow Electroporation System for Solid Tumors, Anticancer Research 33: 2971-2976, 2013.*
Geng et al, Transfection of cells using flow-through electroporation based on constant voltage, Nature Protocols vol. 6, pp. 1192-1208(2011).*
Geng et al, Flow-through electroporation based on constant voltage for large-volume transfection of cells, Journal of Controlled Release 144 (2010) 91-100.*
Zhan et al, Electroporation of Cells in Microfluidic Droplets, Anal. Chem. 2009, 81, 2027-2031.*
Huang and Rubinsky, Flow-Through Micro-Electroporation Chip for Genetic Engineering of Individual Cells, Solid-State Sensors, Actuators, and Microsystems Workshop Hilton Head Island, South Carolina, Jun. 2-6, 2002, p. 198-201.*
Benecia et al, Whole tumor antigen vaccination using dendritic cells: Comparison of RNA electroporation and pulsing with UV-irradiated tumor cells, Journal of Translational Medicine 2008, pp. 1-14.*
Wculek, S.K., et al., "Effective cancer immunotherapy by natural mouse conventional type-1 dendritic cells bearing dead tumor antigen," Journal for ImmunoTherapy of Cancer, 7(100): p. 1-16 (2019).
Jiang, W., et al., "Functional characterization of interleukin-15 gene transduction into the human natural killer cell line NKL," Cytotherapy, 10(3): 265-274 (2008).
Selmeczi, D., et al., "Efficient large volume electroporation of dendritic cells through micrometer scale manipulation of flow in a disposable polymer chip," Biomed Microdevices, 13: 383-392 (2011).

(Continued)

*Primary Examiner* — Maria Marvich
(74) *Attorney, Agent, or Firm* — Harness Dickey & Pierce P.L.C.

(57) ABSTRACT

Methods for preparing antigen-loaded dendritic cells (DCs) for treatment of cancer in a subject are provided, using an electroporation apparatus having an electroporation chamber including an upper electrode, a lower electrode and a path defined in the electroporation chamber. The electroporation apparatus includes a first input allowing passage of DCs into the electroporation chamber and a first output allowing passage of antigen-loaded DCs from the electroporation chamber. The first input and the first output are separated by an offset distance. Methods of treating cancer by administering antigen-loaded DCs are also provided.

20 Claims, 20 Drawing Sheets
(4 of 20 Drawing Sheet(s) Filed in Color)

(56) References Cited

OTHER PUBLICATIONS

Boissel, L., et al., "Transfection with mRNA for CD19 specific chimeric antigen receptor restores NK cell mediated killing of CLL cells," Leuk Res., 33(9): 1255-1259 (2009).
MaxCyte, "MaxCyte VLX® Large-Scale Transfection System," (2017).
MaxCyte, "ExPERT GTx," (2020).
MaxCyte, "ExPERT STx," (2020).

* cited by examiner

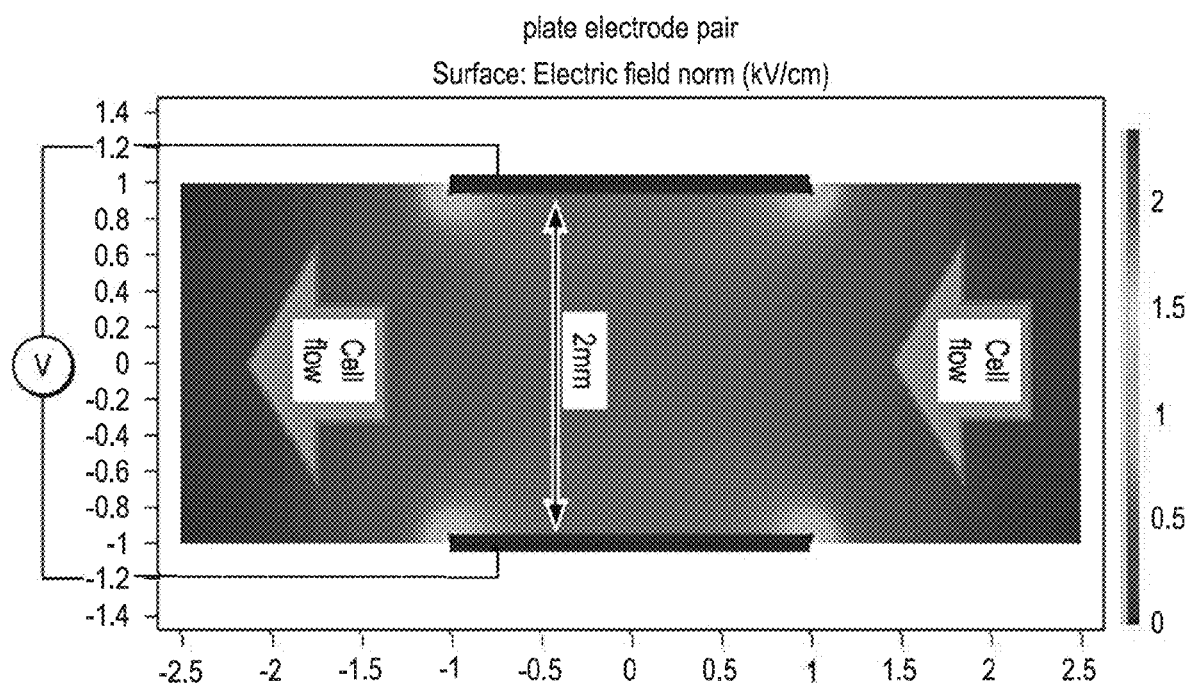
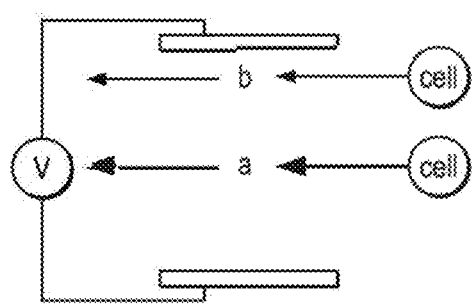
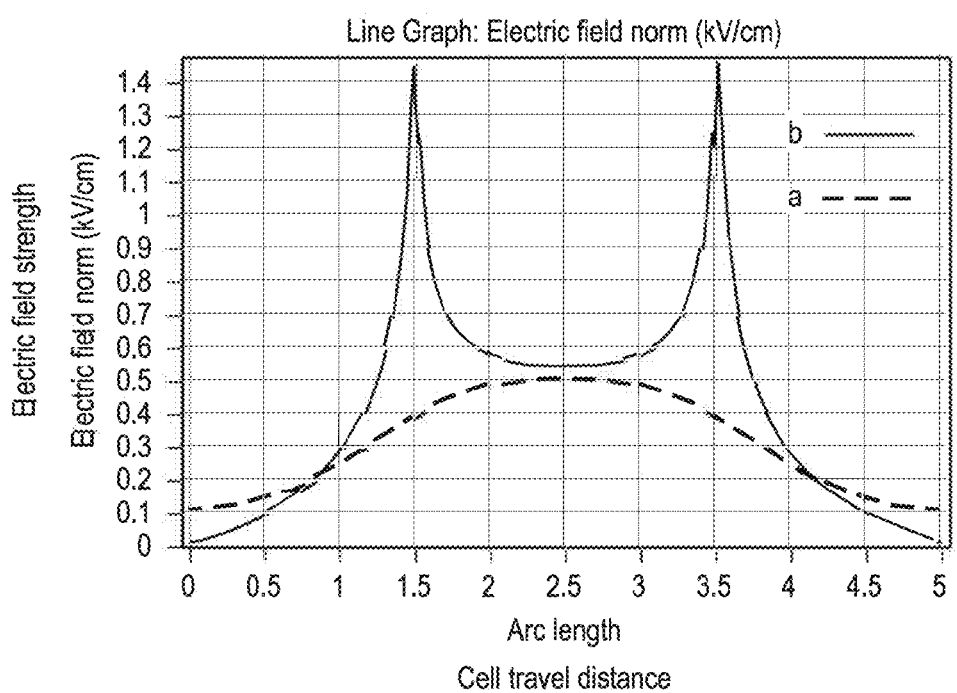
FIG. 1A

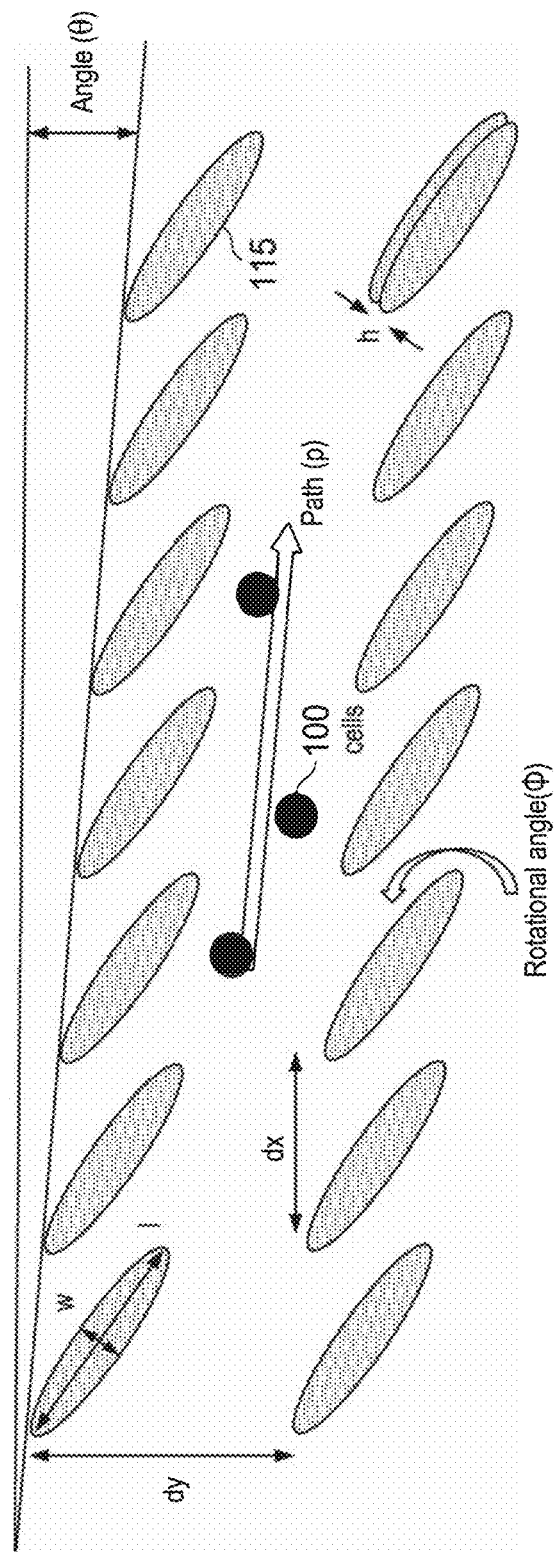
FIG. 2M
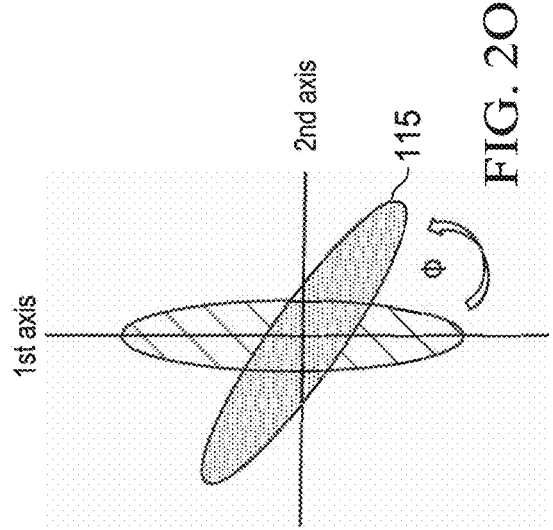
FIG. 2O
FIG. 2N

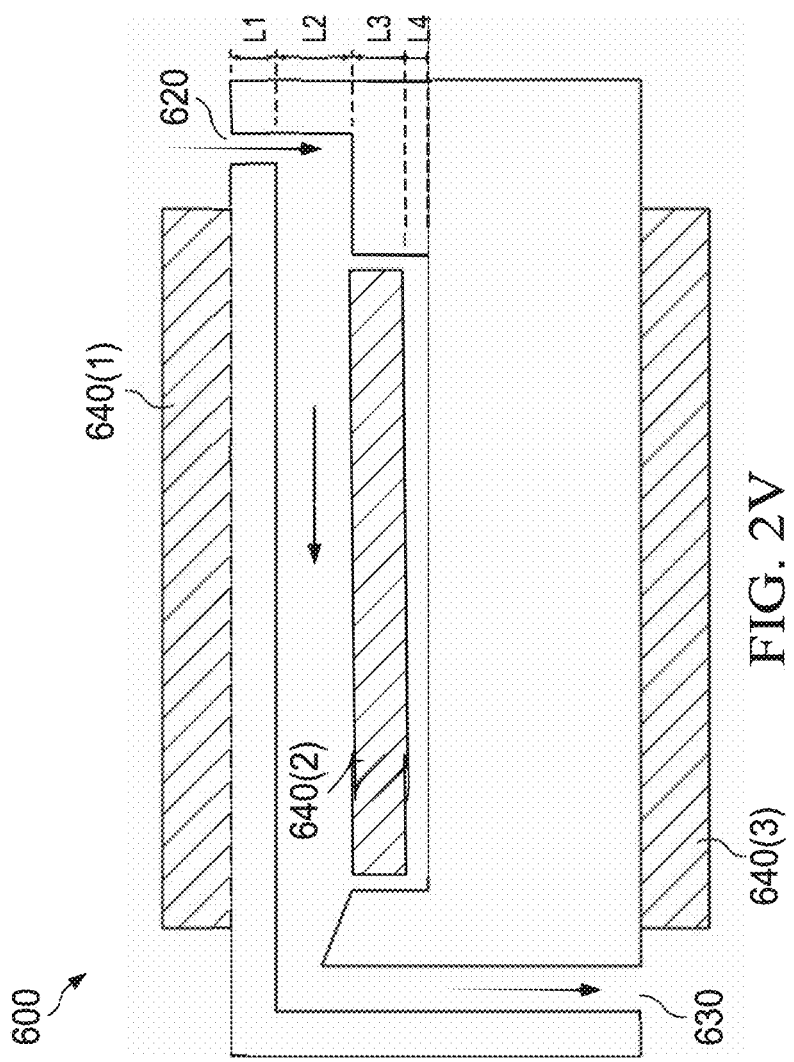

|  | Channel Offset Electroporation Device | Prior Art |
|---|---|---|
| Configuration | Offset | Regular |
| Buffer | Cw100: 110mS/m, 128 mOSM/L | BTX T media: 8mS/m, 270mOSM/L |
| Cell line, density | NK cell ($1.7 \times 10^7$ cells/ml)<br>EC.7 ($4 \times 10^7$ cells/ml) | Dendritic cell ($1 \times 10^7$ cells/ml) |
| Average flow rate | 0.44mL/min | 0.45mL/min |
| Pulse shape | Exponential discharging waveform | Square waveform |
| Number of pulses | 4 | 1 |
| Flow scheme | Stepping (see below) | Continuous |

FIG. 3

METHODS OF PREPARING CANCER TREATMENTS AND METHODS OF TREATING CANCER

CROSS-REFERENCE TO RELATED APPLICATIONS

This application claims the benefit of and priority to U.S. Provisional Application No. 62/947,819, filed on Dec. 13, 2019, the entire contents of which are hereby incorporated herein by reference.

FIELD OF THE INVENTION

The field of the invention relates to methods of preparing a cancer treatment and methods for treating cancer, and in particular, electroporation systems and methods for preparing an antigen-loaded dendritic cell for treatment of cancer, for example, in a cancer vaccination.

BACKGROUND OF THE INVENTION

The background description includes information that may be useful in understanding the methods and techniques presented herein. It is not an admission that any of the information provided herein is prior art or relevant to the subject matter presented herein, or that any publication specifically or implicitly referenced is prior art.

Transfection may be used to introduce nucleic acids into cells to produce genetically modified cells. Various physical and chemical methods exist for transfecting cells, including optoperforation, polymer based methods utilizing calcium phosphate, microinjection, electroporation, and lipid mediated methods (e.g., using liposome-DNA complexes).

Transfection of cells can be used to prepare immunotherapy based cancer treatments. For example, preparation of a cancer vaccination can involve transfecting extracted dendritic cells (DCs) from a subject with tumor antigens from the subject by contacting the tumor antigens with the DCs in a suitable medium to produce tumor antigen-loaded DCs (Wculek, S. et al. (2019) *Journal for ImmunoTherapy of Cancer*, 7(100):1-16).

Electroporation involves applying a controlled direct current (DC) electrical pulse to a cell for a relatively short duration of time. The electrical pulse is thought to induce a transmembrane potential that causes a reversible breakdown of the ordered structure of a cell membrane, leading to the formation of pores in the membrane. Molecules of interest can then enter the cell through the pores until the pores close, typically within milliseconds to seconds. Pore formation can be controlled by adjusting various parameters, especially gap width (e.g., distance between parallel electrode plates), electrical pulse wave form, electric field strength, temperature, and electrical pulse length.

Electroporation is commonly used at the laboratory scale (e.g., using small cuvettes with a capacity of about 0.5 mL), but such laboratory based techniques are not suitable for large scale, clinical grade production, due to lack of efficiency and high cost. Other transfection methods, such as lipid-based techniques using Lipofectamine 2000™, are also frequently used, but have similar drawbacks due to high cost. Additionally, lipid based methods do not work well with some cell types of clinical interest, e.g., NK cells such as haNKs. NK cells have been transfected using mRNA and electroporation, for example, to genetically manipulate primary NK cells to express chimeric antigen receptors (CARs—see *Leuk Res.* (2009) 33:1255-9) or to express cytokines for autocrine growth stimulation (*Cytotherapy* (2008) 10:265-74). While commercial products exist such as Maxcyte for large scale transfection, e.g., reaction sizes of greater than 1 mL, these products are also expensive and/or lack a high-throughput capability. Similarly, these commercial products are not optimal for transfecting NK cells, often leading to poor yield and/or issues with low cell viability. Typical electroporation rates may yield 2-5% DNA transfection efficiencies with about 10-20% cell viability.

With conventional techniques, as shown in FIG. 1A, electroporation is performed using two parallel plate electrodes. In this configuration, the cells typically flow between the two parallel plates. However, the electric field is non-uniform, with cells in the middle of the chamber, shown as (a), experiencing a more uniform electric field while cells near an electrode, shown as (b), experience a non-uniform electric field and in particular, experience an electric field spike present at the boundary of the electrode. Other techniques utilize parallel plates of micromesh electrodes, as shown in FIG. 1B (Selmeczi, D. et al., "Efficient large volume electroporation of dendritic cells through micrometer scale manipulation of flow in a disposable polymer chip," Biomed Microdevices, 13: 383-392 (2011)), in which the cells pass through an upper micromesh electrode and a lower micromesh electrode. While this technique provides a more uniform electric field than passing between two parallel electrode plates, as shown by the similar trajectories of cells in the middle of the chamber (a) and near the boundary of the chamber (b), the chamber width or distance between the upper micromesh electrode and lower micromesh electrode is limited, leading to a low transfection efficiency. The configurations shown in FIGS. 1A and 1B utilize an electric field strength of about 1-1.3 kV/cm (e.g., 200V/2 mm for parallel plates, 40V/400 um for parallel micromesh electrodes).

In other aspects, single cell electroporation chips have been used for transfection. In this technique, a silicon chip may comprise a plurality of linear channels, with each channel having opposing electrodes placed on opposite sides of the channel. The cells pass through the channel and are exposed to an electric field. With this type of technique, DNA transfection efficiencies of about 68% with cell viability of about 79% have been achieved.

Even though various transfection systems and methods exist for mammalian cells, such techniques suffer from one or more disadvantages. Accordingly, there is still a need to provide improved electroporation systems and methods, especially for high throughput, large scale manufacturing processes.

SUMMARY

The present disclosure is directed to various methods for preparing a cancer treatment and methods for treating cancer, for example, by electroporation of dendritic cells (DCs) in the presence of antigens, such as tumor cell antigens. In particular, the methods for electroporation use an electroporation apparatus including a first input separated from a first output by an offset distance can provide for high efficiency and viability.

In some aspects, a method of preparing antigen-loaded DCs for the treatment of cancer in a subject is provided. The method includes electroporating DCs in the presence of antigens to form antigen-loaded DCs. The DCs are derived from the subject. The electroporating includes flowing the DCs and the antigens into an electroporation chamber. The DCs are suspended in an electroporation medium. The electroporation chamber includes an upper electrode, a lower electrode, and a path defined between the upper electrode and the lower electrode for the DCs and the antigens to flow. The upper electrode is bounded by a first material and the lower electrode is bounded by a second material. The first material includes a first input allowing passage of DCs and antigens into the electroporation chamber, and the second material includes a first output allowing passage of antigen-loaded DCs from the electroporation chamber. The first input and the first output are separated by an offset distance.

In another aspect, antigen-loaded DCs prepared by the methods described herein are provided.

In another aspect, a method of treating cancer is provided. The method includes administering to a subject antigen-loaded DCs prepared by the methods described herein.

In some aspects, electroporation protocol involves subjecting DCs to multiple electrical pulses, a stepping fluid flow, a low conductivity and low osmolarity electroporation buffer, relatively moderate capacitance, and/or a relatively moderate time constant.

Various objects, features, aspects and advantages of the subject matter described herein will become more apparent from the following detailed description of preferred embodiments, along with the accompanying drawing figures in which like numerals represent like components.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B show conventional electroporation devices including parallel plate electrodes (as shown in FIG. 1A) and micromesh electrodes with no offset between the input and the output (as shown in FIG. 1B).

FIG. 2A shows an illustration of the structure of the input output chamber offset electroporation device. FIG. 2B shows an illustration of the electric field of the input output chamber offset electroporation device. FIG. 2C shows the electric field strength as a function of cell traveling distance through the input output chamber offset electroporation device. FIG. 2D shows an alternative configuration of an electroporation apparatus according to some embodiments provided herein.

FIGS. 2M-2S are illustrations showing various aspects of the geometry and positioning of posts within the chamber according to some embodiments provided herein.

FIGS. 2V and 2W show alternative configurations of an electroporation apparatus according to some embodiments provided herein.

FIG. 3 shows a table of parameters associated with the chamber offset electroporation device, according to some embodiments provided herein.

DETAILED DESCRIPTION

Figure 1B:
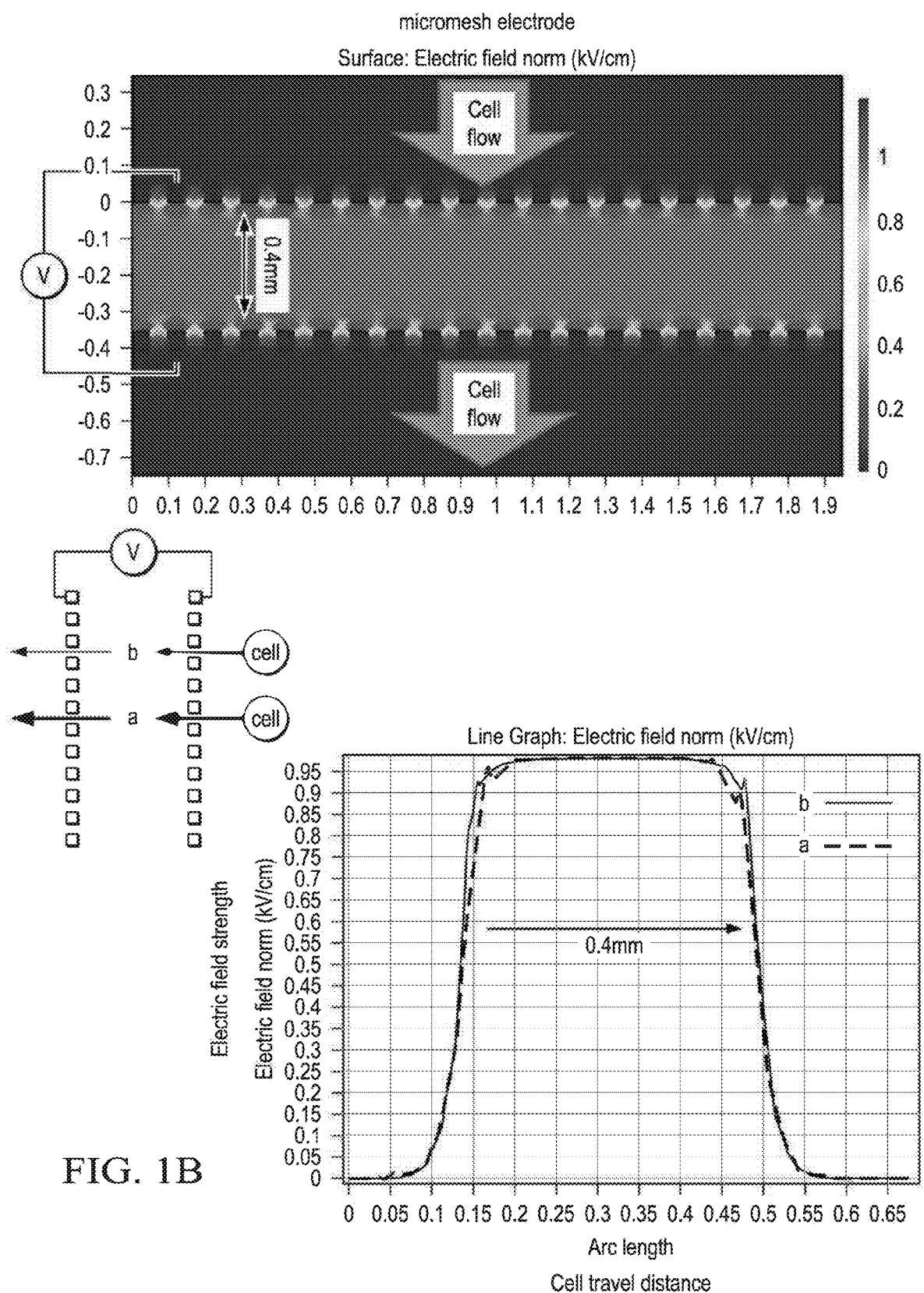

Systems and methods are provided for electroporation of cells, for example, mammalian cells, such as dendritic cells (DCs), using an electroporation apparatus having a first input separated from a first output by an offset distance. In particular, DCs from a subject can be electroporated with antigens, for example, tumor antigens derived from the subject, to form antigen-loaded DCs. Electroporation protocols that provide for high efficiency and viability are provided. In some aspects, the electroporation protocol involves subjecting cells to multiple electrical pulses, a stepping fluid flow, a low conductivity and low osmolarity electroporation buffer, relatively moderate capacitance, and/or a relatively moderate time constant. In various aspects, these antigen-loaded DCs can be used for treating cancer, for example, as a cancer vaccination, by administering the antigen-loaded DCs to the subject.

In various aspects, an apparatus for electroporating DCs with antigens is provided. The apparatus can include one or more electroporation chambers, wherein each electroporation chamber includes an upper electrode, a lower electrode, and a path defined between the upper electrode and the lower electrode for the DCs and antigens to flow. The upper electrode and the lower electrode each can be a sheet electrode, a mesh electrode (e.g., micromesh electrode), or a combination thereof.

In some embodiments, the upper electrode can have a first porosity and the lower electrode can have a second porosity. The first porosity can allow for passage of the DCs and the antigens from the first input through the upper electrode into the electroporation chamber. The second porosity can allow for passage of the antigen-loaded DCs through the lower electrode and the first output from the electroporation chamber. For example, an upper electrode and lower electrode can each have a porosity (e.g., first porosity, second porosity) of open area of about 30% to about 50%. A width of a pore opening of an upper electrode and a lower electrode can be about 70 µm to about 140 µm. Additional details concerning apparatuses suitable for practicing the methods described herein can be found in co-pending international patent publication no. WO 2020/014264, the entire contents of which are herein incorporated by reference.

The upper electrode can be bounded by a first material, and the lower electrode can be bounded by a second material. The first material includes a first input allowing passage of DCs into the electroporation chamber, and the second material includes a first output allowing passage of electroporated cells from the electroporation chamber. As used herein, "electroporated cells" include antigen-loaded DCs, dead DCs, and non-transfected DCs. The first input and the first output are separated by an offset distance. Additionally or alternatively, instead of the DCs and/or the antigens traveling through pores of the upper electrode to enter the electroporation chamber, the upper electrode may optionally include a second input to allow passage of DCs and/or the antigens into the electroporation chamber. The second input may be substantially aligned with the first input in the first material. Additionally or alternatively, instead of the electroporated cells traveling through pores of the lower electrode to exit the electroporation chamber, the lower electrode may include a second output to allow passage of electroporated cells out of the electroporation chamber. The second output may be substantially aligned with the first output in the second material.

Figure 2A:
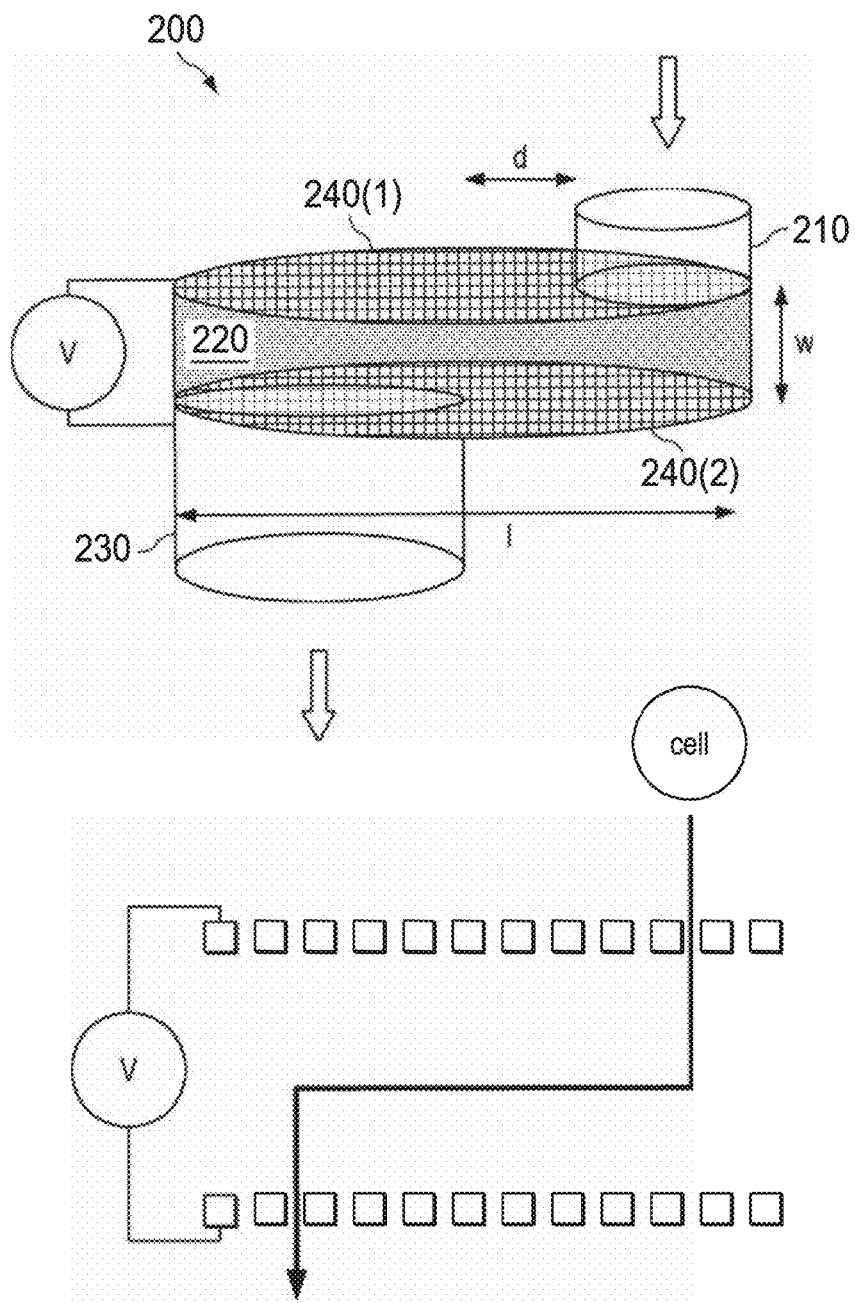
FIGS. 2A-2D show aspects of an apparatus for electroporation including an electroporation device according to some embodiments provided herein.

For example, FIG. 2A illustrates an exemplary apparatus for electroporating DCs with antigens, which includes an IOCO electroporation device 200. The IOCO electroporation device 200 comprises two electrodes, an upper electrode 240(1) and a lower electrode 240(2), shown here in alignment with one another. The upper surface of the upper electrode 240(1) may be bounded a first material and the lower surface of the lower electrode 240(2) may be bound be a second material. For example, the first material and the second material may be a non-porous material, e.g., such as polydimethylsiloxane (PDMS) acrylic, polyethylene, polypropylene, to contain cells within the interior chamber of the electroporation device, and in particular, within the chamber 220 between the two parallel micromesh electrodes. A first input 210 is formed (a region without PDMS) on the upper electrode 240(1), and a first output 230 is formed (a region without PDMS) on the lower electrode 240(2). Thus, in this example, the upper and lower electrodes 240(1) 240 (2) span the length of the electroporation chamber 220, bounded by a first material (an upper PDMS layer) and a second material (a lower PDMS layer), to direct the flow of cells along a lateral distance of the chamber. An opening (first input 210) in the first material (upper PDMS layer) and an opening (first output 230) in the second material (lower PDMS layer) is separated by an offset distance (d) to facilitate flow of cells laterally through the electroporation chamber 220.

In any embodiment, an electroporation chamber may have any desired shape, including but not limited to circular, oval, square, rectangular, or a polygon.

In any embodiment, an electroporation chamber width (w) may range from about 0.01 mm to about 5 mm, about 0.05 mm to about 5 mm, about 0.1 mm to about 5 mm, about 1 mm to about 5 mm, about 2 mm to about 5 mm, about 0.01 mm to about 4 mm, about 0.1 mm to about 4 mm, about 1 mm to about 4 mm, about 0.01 mm to about 2 mm, about 0.05 mm to about 1 mm, about 0.1 mm to about 0.5 mm, or about 0.2 mm to about 0.4 mm. In some aspects, the chamber width (w) is about 0.3 mm.

In some aspects, an offset distance (d) may range from about 0.1 cm to about 10 cm, from about 0.1 cm to about 5 cm, from about 0.1 cm to about 4 cm, from about 1 cm to about 3 cm, In some aspects, the offset distance (d) about 2 cm. In some aspects, there is no overlap between the input and the output.

The first input and/or second input are in fluid communication with the electroporation chamber, and the electroporation chamber is in fluid communication with the first output and/or second output. The input(s), output(s), and electroporation chamber may additionally comprise one or more valves, regulators, pumps, or any other microfluidic components, for controlling the flow of cells through the electroporation chamber.

In some aspects, both the first input and first output may be positioned in the first material on the upper electrode, provided that a suitable offset distance is maintained between the first input and the first output. Additionally or alternatively, both the second input and the second output may be present in the upper electrode. In other aspects, both the first input and first output may be positioned in the second material on the lower electrode, provided that a suitable offset distance is maintained between the first input and the first output. Additionally or alternatively, both the second input and the second output may be present in the lower electrode.

In some embodiments, the DCs may enter the first input flowing in a first direction. Once passing through the upper electrode, the flow of the cells can change direction, flowing laterally in a path along the length of electroporation chamber in a direction perpendicular or substantially perpendicular to the first direction. Once reaching the first output, the flow of the cells can change direction again, exiting the electroporation chamber, in a second direction parallel to the first direction.

In some aspects a voltage is applied across the parallel electrodes, suitable to produce an electric field in the range from about 0.3 kV/cm to about 3 kV/cm. Typical electric fields range from about 1-1.3 kV/cm (e.g., 40V/300 um) for haNKS, and about 0.3-1 kV/cm for EC-7 cells. In some aspects, the voltage may be about 10V, about 20V, about 30V, about 40V, about 50V, about 75V, about 100V, or about 200V, or any suitable range therein, or more.

In some aspects, the diameters of the first input, the second input, the first output and the second output may be about the same. In other aspects, the diameter of the first input may be greater or lesser than the diameter of the first output and/or the diameter of the second input may be greater or lesser than the diameter of the second output. For example, the diameter of the first input and/or the second input may range from about 0.1 mm to about 10 mm, from about 1 mm to about 7 mm, from about 3 mm to about 5 mm, or may be about 4 mm. The diameter of the first output and/or the second output may range from about 0.1 mm to about 10 mm, from about 1 mm to about 7 mm, from about 3 mm to about 5 mm, or may be about 4 mm.

In any embodiment, a length (l) of the electroporation chamber may range from about 2 mm to about 100 mm, about 2 mm to about 80 mm, about 2 mm to about 60 mm, about 2 mm to about 40 mm, about 2 mm to about 20 mm, from about 5 mm to about 15 mm, from about 8 mm to about 12 mm, or may be about 10 mm.

In any embodiment, a ratio of length (l) to width (w) (l/w) can be about 1 to about 50, about 1 to about 40, about 1 to about 20 or about 1 to about 10.

Figure 2B:
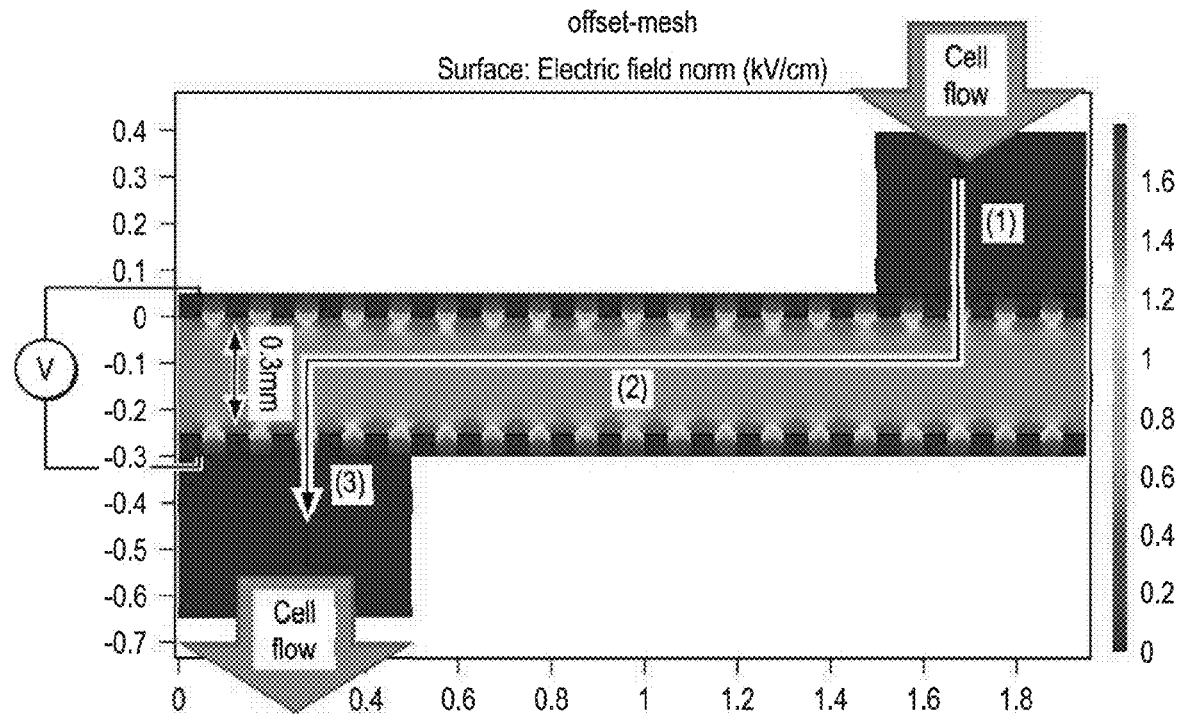

FIG. 2B is an illustration of the electric field in the IOCO electroporation device 200. Once the DCs enter the electroporation chamber, at least a portion or all of the DCs are exposed to a uniform electric field, until exiting the electroporation chamber. Position (1) refers to a cell in the input (first input 210), position (2) refers to a cell in the electroporation chamber, and position (3) refers to a cell in the output (first output 230).

Figure 2C:
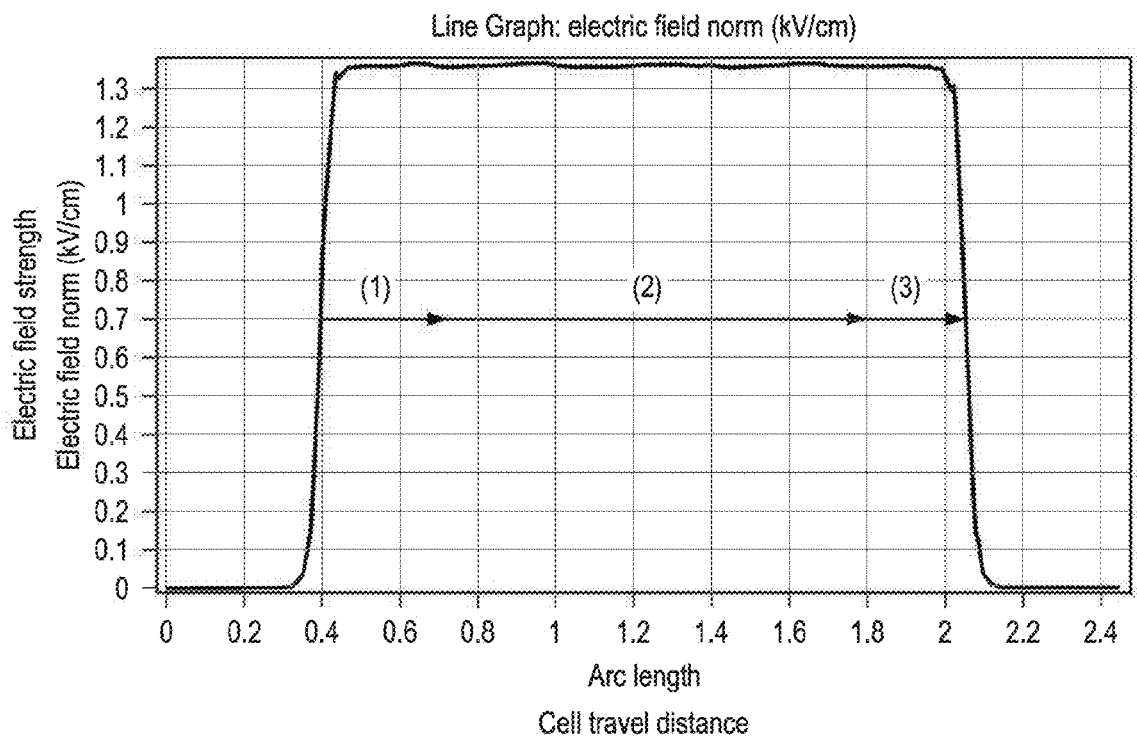

FIG. 2C is a plot of the electric field strength versus cell travel distance through the IOCO electroporation device 200. DCs in the input (first input 210), shown at position (1), are not exposed to an electric field until they have passed through the electrode into the electroporation chamber. Within the electroporation chamber, shown as position (2), at least a portion or all of the DCs experience a uniform (maximum strength) electric field while traveling along the length of the chamber. Once in the output (first output 230), shown at position (3), DCs are not exposed to an electric field.

Figure 2D:
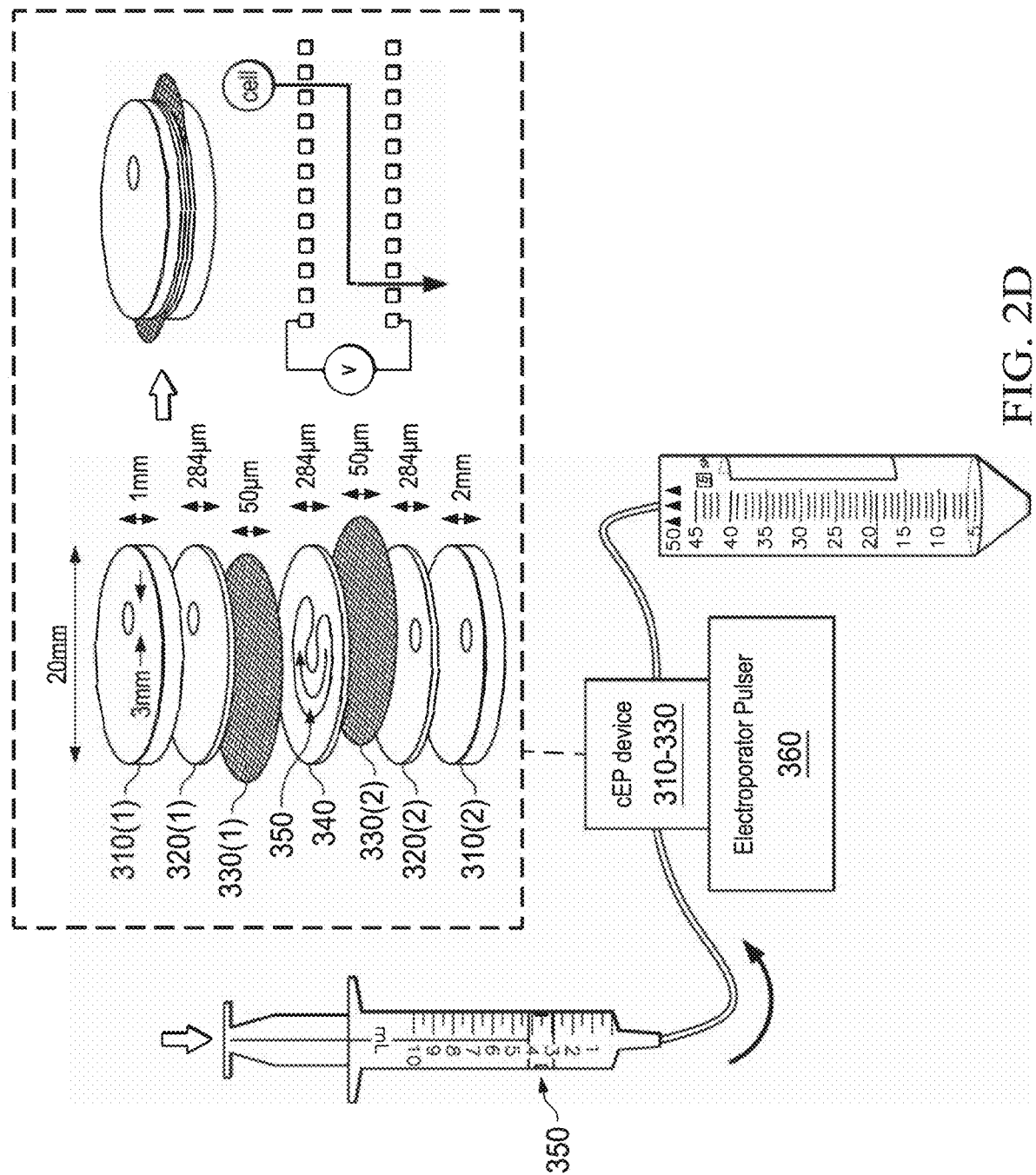

FIG. 2D shows an alternative configuration of an electroporation apparatus presented herein including an electroporation device 310-330. In this embodiment, instead of having a linear (horizontal) flow path between the upper and lower electrodes, the DCs may take a curved or circular (horizontal) flow path between the upper and lower electrodes. The linear flow path and the curved flow path may each include at least one segment that extends parallel to a plane defined by a surface of at least one of the upper and lower electrodes.

In this example, the various layers of an electroporation device 310-330 are shown in FIG. 2D. Solid outer plates 310(1) and 310(2) (e.g., plastic, metal, or any other suitable material) encapsulate the device. An adhesive layer or other suitable material (e.g., double sided tape, pressure sensitive adhesive material, etc.) 320(1) (first material) is placed between the upper solid outer plate 310(1) and the upper mesh 330(1), and an adhesive layer or other suitable material (e.g., double sided tape, pressure sensitive adhesive layer, etc.) 330(2) (second material) is placed between the lower outer plate 310(2) and the lower mesh 330(2). Another adhesive layer (e.g., pressure sensitive adhesive material or double sided tape, etc.) (340) comprising a curved channel or curved path 335 through which the cells and cargo may flow is positioned between the upper and the lower meshes 330(1) 330(2). Fluid may be driven through the electroporation device 310-330 by a syringe 350. The electroporation device 310-330 may also interface with an electroporator pulser 360. In any embodiment, the electroporation device 310-330 may be a continuous electroporation device wherein cells flow through the device in a continuous manner.

Figure 2E:
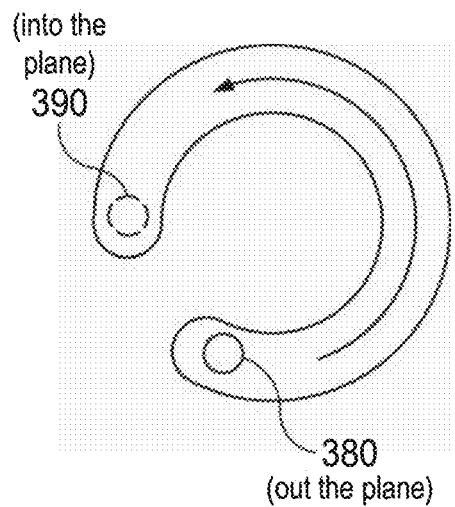
FIGS. 2E-2G show aspects of a path in an electroporation chamber according to some embodiments provided herein.
Figure 2F:
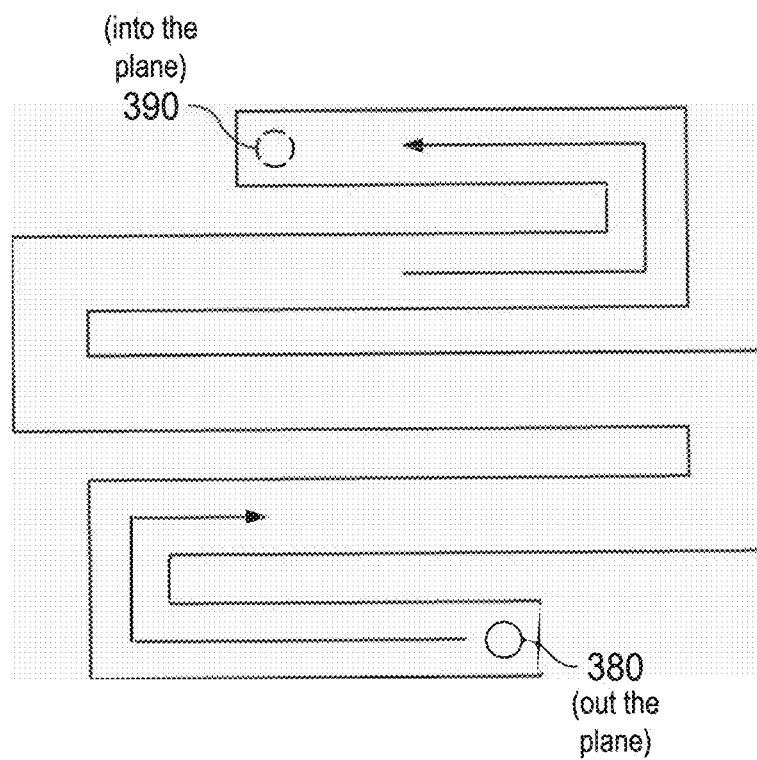
Figure 2G:
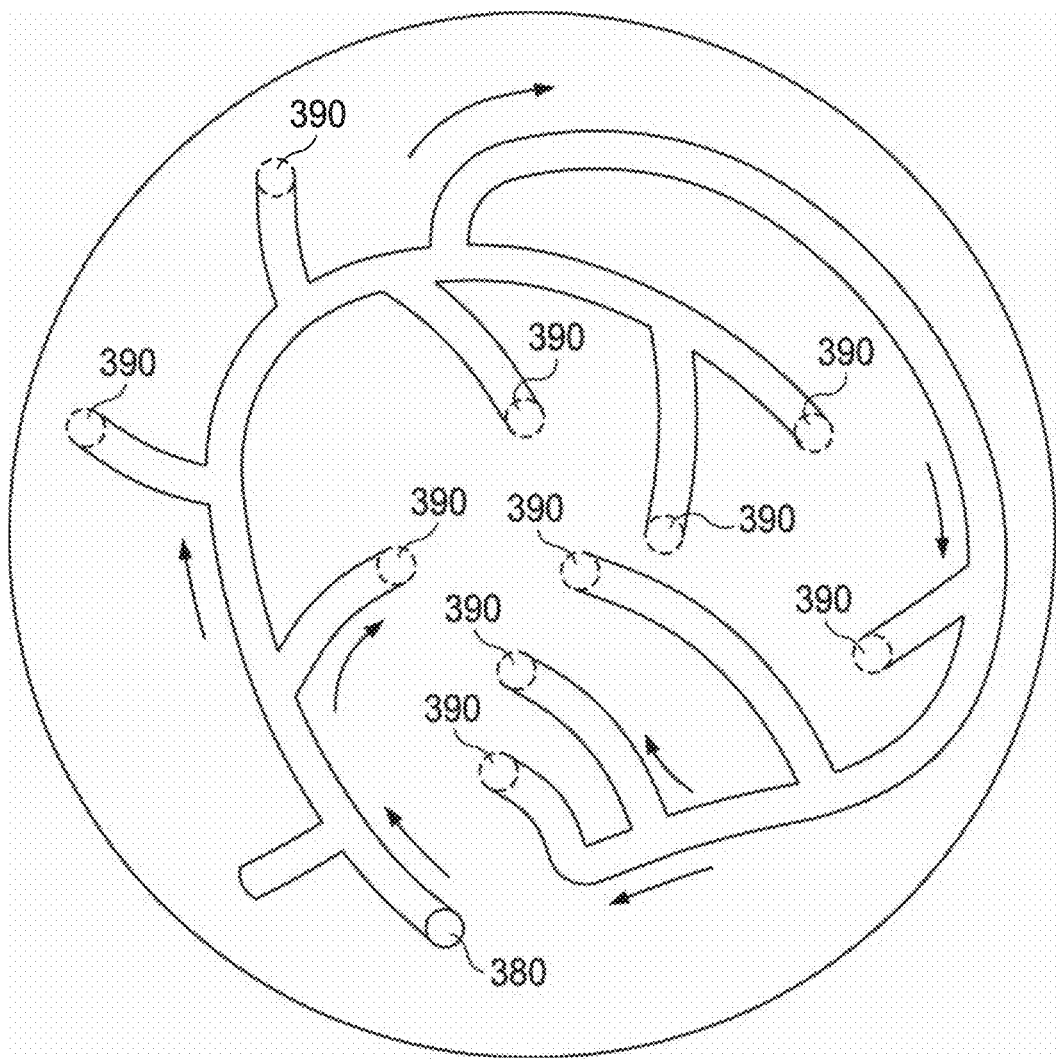

A path for the DCs and the antigens to flow through the electroporation chamber is defined in the electroporation chamber, for example, between the upper electrode and the lower electrode. It is understood that any suitable path, provided that the path includes at least one horizontal flow segment that is parallel to at least one of the upper electrode and the lower electrode, are contemplated by the embodiments provided herein. The horizontal flow segment may form greater than or less than any of 1/10, 1/4, 1/2, 3/4, 7/8, or 9/10 of the length of the path extending between the upper and lower electrode. In some cases, the path may be linear, curved, branching, circuitous, tortuous, or any combination thereof. Examples of a curved path include, but are not limited to a circular path, a spiral path, a conical path, or any combinations thereof. For example, as illustrated in the FIG. 2B, a path is linear where arrows illustrate flow of cells. As illustrated in FIGS. 2D and 2E, a path is curved where arrows illustrate flow of cells. As illustrated in FIG. 2F, a path may be linear with one or more changes in direction or switch-backs with arrows illustrating flow of cells. As illustrated in FIG. 2G, a path may be circular and have one or more branches. As shown in FIGS. 2E-2G, the paths may include an inlet 380 (out of the plane), which may correspond to the first input or be substantially aligned with the first input, and one or more outlets 390 (into the plane), which may correspond to the first output or be substantially aligned with the first output. The length of the path may be adjusted, e.g., shortened or lengthen, depending upon the particular characteristics of the electroporation process.

Figure 2H:
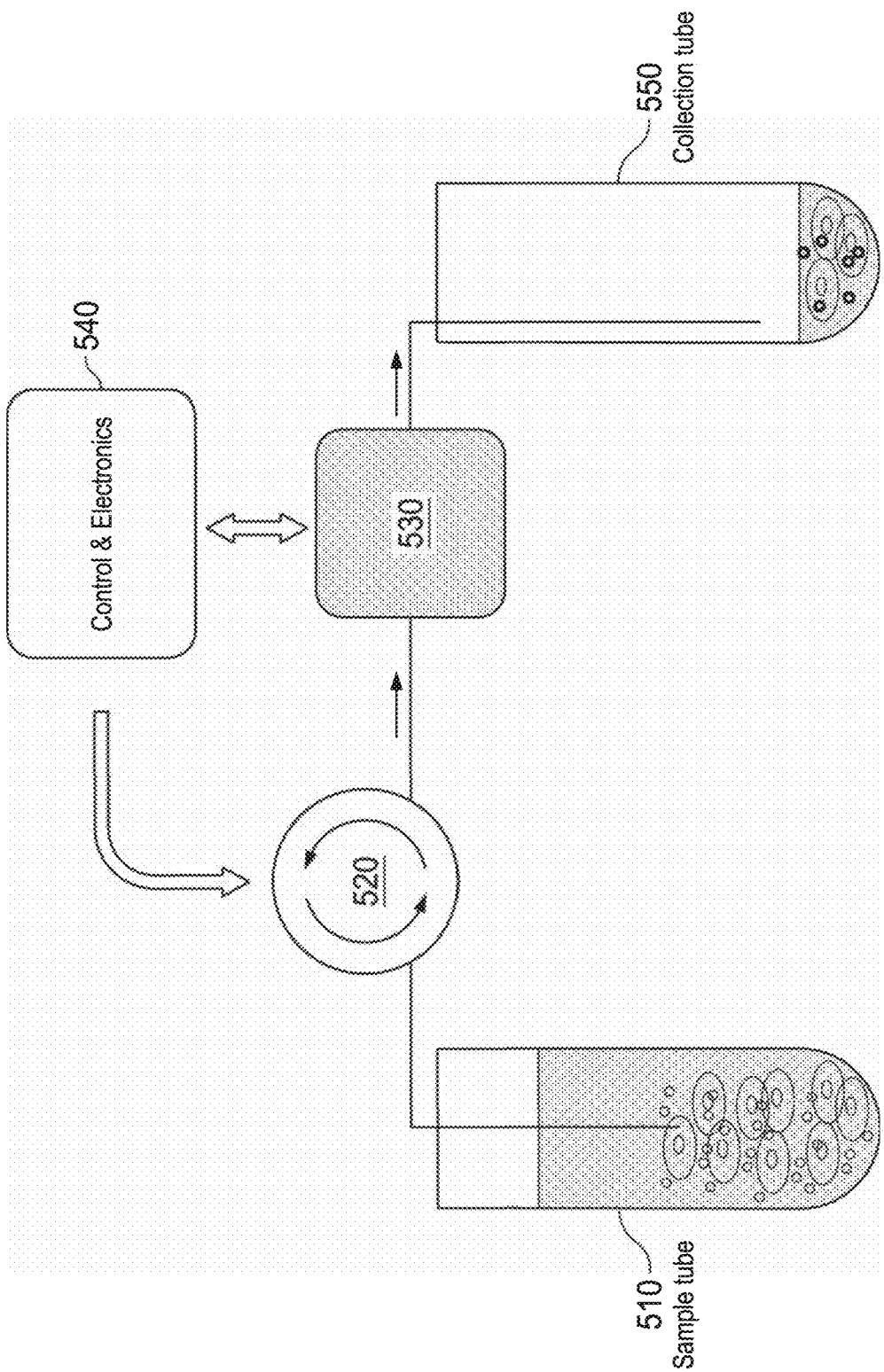
FIGS. 2H-2J show alternative configurations of an electroporation apparatus according to some embodiments provided herein.

In any embodiment, the electroporation apparatuses described herein may include a means for generating flow of cells from a sample tube into an electroporation chamber of an electroporation device and flow through the device into a collection tube. For example, as illustrated in FIG. 2H, a flow generating means 520 is in fluid communication with a sample tube 510 containing cells and/or cargo for transfection and an electroporation device 530. The flow generating means 520 can generate flow of the DCs and antigens from the sample tube 510, through the electroporation device 530 and into collection tube 550. The flow generating means may be any suitable pump, for example, a peristaltic pump or a syringe pump. It is contemplated herein that more than one flow generating means 520 may be present in an electroporation apparatus. For example, one or more flow generating means 520 may present between and in fluid communication with the sample tube 510 and the electroporation device 530 and one or more flow generating means 520 may present between and in fluid communication with the collection tube 550 and the electroporation device 530. Additionally or alternatively, the electroporation device 530 and/or the flow generating means 520 may also interface with a controller 540, for example, including an electroporator pulser.

Figure 2I:
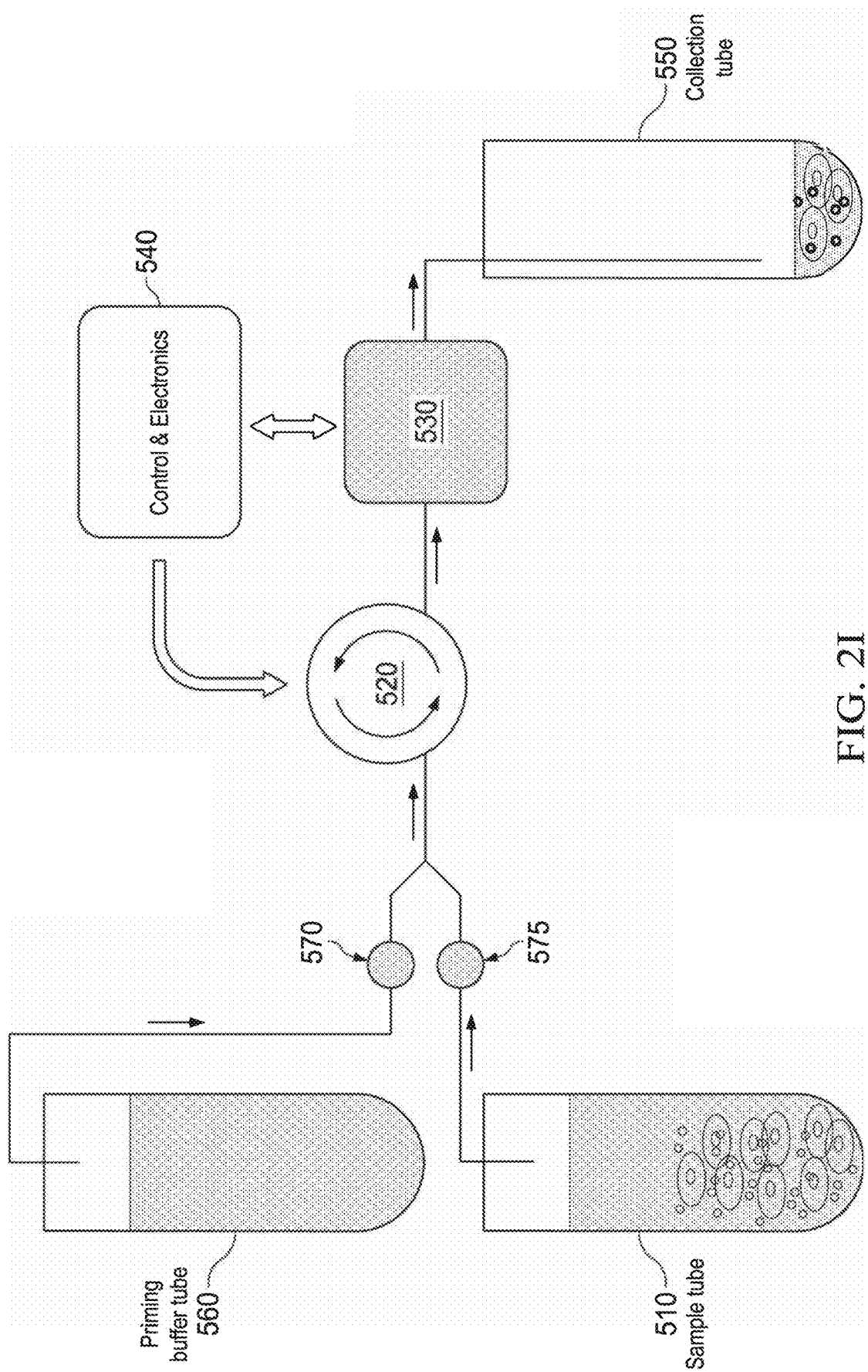

In any embodiment, the electroporation apparatuses described herein may also include a priming buffer tube in fluid communication with the electroporation device to deliver priming buffer as needed. Examples of a suitable priming buffer include, but are not limited to distilled water, deionized water, isotonic buffer, and combinations thereof. For example, as illustrated in FIG. 2I, a priming buffer tube 560 is in fluid communication with electroporation device 530. A valve 570 may be opened to deliver priming buffer to the electroporation device 530 via flow generating means 520 or the valve 570 may be closed to stop delivery. A valve 575 may be opened to deliver cells and/or cargo to the electroporation device 530 via flow generating means 520 or the valve 575 may be closed to stop delivery. In some embodiments, valves 570 and 757 both may be opened to deliver cells and priming buffer. In some embodiments, priming buffer may be delivered first followed by delivery of DCs and/or antigens.

Figure 2J:
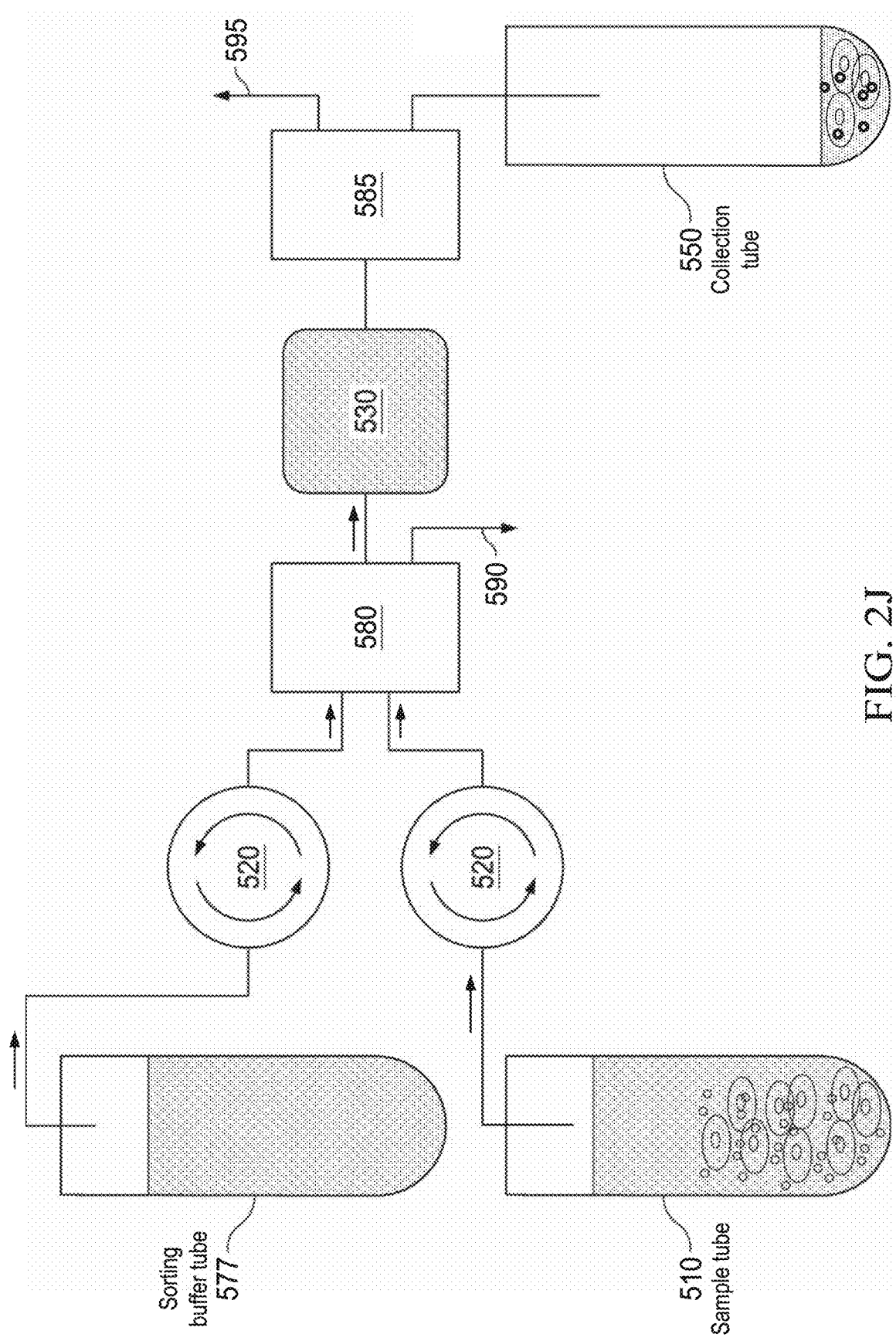

In any embodiment, the electroporation apparatuses described herein may also include a first microfluidics device for sorting the DCs prior to entering an electroporation chamber of an electroporation device. For example, as illustrated in FIG. 2J, a first microfluidics device 580 can be in fluid communication with an electroporation device 530, a sample tube 510 containing DCs for transfection, and optionally a buffer sorting tube 577. Flow generating means 520 can generate flow of the DCs from the sample tube 510 and/or buffer from sorting tube 577 through the electroporation device 530 and into a collection tube 550. The first microfluidics device 580 is capable of pre-sorting DCs, for example based on size of cells, from the sample tube 510 to the electroporation device 530. Additionally or alternatively, the first microfluidics device 580 is capable of accomplishing a buffer change of the cells from the sample tube 510. Stream 590 contains DCs sorted out and not delivered to the electroporation device 530 can either be a waste stream or sent to another electroporation device with different parameters. Additionally or alternatively, a second microfluidics device 585 can be in fluid communication with the electroporation device 530 and collection tube 550. The second microfluidics device 585 is capable of sorting electroporated cells, for example based on size of the electroporated cells, prior to collection in the collection tube 550. Stream 595 contains the electroporated cells sorted out and not delivered to the collection tube 550.

Although, two microfluidics devices are shown in FIG. 2J, it is contemplated herein that only one microfluidics device may be present in an electroporation apparatus, for example, to sort cells prior to entering an electroporation chamber or to sort electroporated cells exiting an electroporation chamber.

Figure 2K:
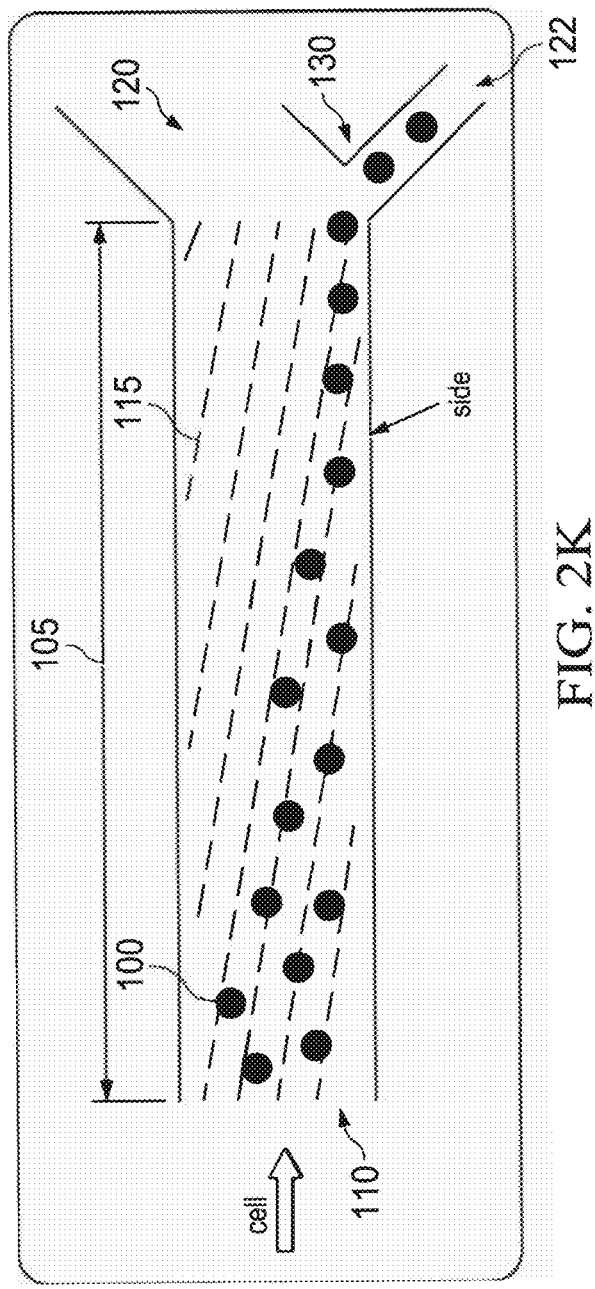
FIGS. 2K-2L illustrate example microfluidics chambers for sorting cells according to some embodiments provided herein.
Figure 2L:
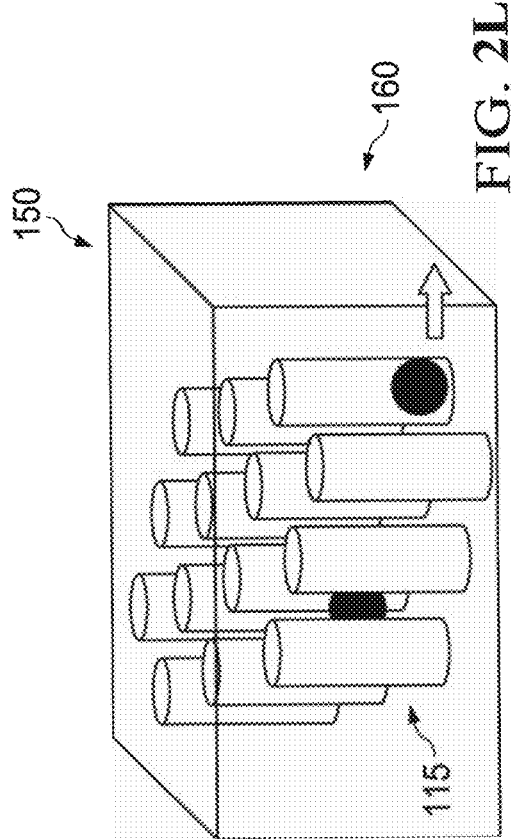

FIG. 2K is an illustration of an example microfluidics device (e.g., microfluidics device 580, microfluidics device 585). In this example, a solution comprising cells 100 (e.g., DCs for transfection, electroporated cells, antigen-loaded DCs) enters a chamber 105 at input mechanism 110. Cells are illustrated as circles. The cells pass through chamber 105, which comprises a matrix of posts 115, shown here as rectangular structures distributed along a plurality of lines having a slope. As the cells pass in between the diagonally oriented rows of posts in the chamber, the cells are deflected laterally, towards a second output mechanism 122. A side view of a portion of the chamber is shown in FIG. 2L, wherein the chamber has a floor 160 and optionally has a ceiling 150, which may be of the same material as the posts 115 or a different material. Cells (black circles) are shown flowing through the matrix of posts. It is understood that the rows of posts may also be arranged in a curvilinear manner, which would also result in the cells being directed towards a side of the chamber.

In this example, two output mechanisms are shown for the chamber. The solution that exits the chamber via first output mechanism 120 (also can be referred to as a third output mechanism, when more than one microfluidics device is present) is depleted of cells, while the solution that exits the chamber via second output mechanism 122 (also can be referred to as a fourth output mechanism when more than one microfluidics device is present) is enriched in cells. In any embodiment, the second output mechanism can be in fluid communication with an electroporation chamber, for example, with a first input. Depletion refers to a state in which the concentration of cells in the solution exiting the chamber via output mechanism 120 has been reduced by 50%, 60%, 70%, 80%, 90%, 95%, 96%, 97%, 98%, or 99% as compared to the concentration of cells in the solution entering the chamber at input mechanism 110. Enrichment or concentration refers to a state in which the concentration of cells in the solution exiting the chamber via output mechanism 122 has been increased by 50%, 100%, 200%, 300%, 400%, 500%, 600%, 700%, 800%, 900%, 1000% or more as compared to the concentration of cells in the solution entering the chamber at input mechanism 110. For the cells to be directed to output mechanism 122, the deflection point 130 of the chamber should be situated such that exiting cells are routed to output mechanism 122 (and not output mechanism 120). In general, output mechanism 122 is configured to have a larger cross sectional area than output mechanism 120. In general, the output mechanisms will have a cross sectional area large enough for fluid flow at the flow rates described herein, without producing high pressures which would damage the cells or the device.

In some embodiments, the width of output mechanism 120 is greater than the width of output mechanism 122. For example, the width of output mechanism 120 is 1.5×, 2×, 2.5×, 3×, 3.5×, 4×, 4.5×, 5×, 5.5×, 6×, 6.5×, 7×, 7.5×, 8×, 8.5×, 9×, 9.5× the width of output mechanism 122. In other embodiments, the sum of the cross-sectional areas of the output mechanisms may be equal to or greater than the sum of the cross-sectional areas of the input mechanisms.

In some embodiments, the microfluidics device is configured to allow a standard pump or a syringe or the like to be connected to the microfluidics device to flow a solution comprising cells through the device. Parameters that can influence the flow of a solution though a device include the dimensions of the chamber 105, the in plane and out of plane dimensions of the posts 115, the spacing of the posts within a row (dx), the rotation of the posts ($\phi$), the distance between rows of posts (dy), the diameter of the input mechanism, and the diameters of the output mechanisms (see, FIGS. 2M-2Q below). In some embodiments, dimensions of these parameters are selected to be compatible with applied pressure from manual operation of syringes or standard pumps (e.g., peristaltic pumps, diaphragm pumps, syringe pumps, lobe pumps, etc.) that drive flow of the solution through the device. A range of pressures are permitted, provided that the pressure does not damage the microfluidics device or the cells.

In general, cells may flow into the microfluidic device in a series (one at a time and into a particular path) or in multiples (multiple cells that flow into multiple paths).

FIG. 2M is an illustration of a top-down view of a section of chamber 105, wherein the section includes two rows of seven posts each. Cellular flow is shown along path (p). This illustration shows the positioning of posts 115 in a section of the chamber of the microfluidics device. In general, the posts are aligned along lines having a slope as defined by angle ($\theta$) at a spacing interval (dx), which may be fixed or variable, provided that the variation does not lead to cells escaping from the path (p) between the posts.

In some embodiments, the width of the chamber is 1 mm, 2.5 mm, 5 mm, 7.5 mm, 10 mm, 12.5 mm, 15 mm, 17.5 mm, 20 mm, 30 mm, 40 mm, 50 mm, or more, or any size in between. The width of the individual paths (p) controls the characteristics of the streamlines. Any number of paths, e.g., 1, 2, 4, 8, 12, 16, 32, etc., or any range in between, may be employed depending on the width of the chamber. In other embodiments, the flow rate of fluid through the chamber may be 1 mL/hr, 2 mL/hr, 3 mL/hr, 4 mL/hr, 5 mL/hr, 6 mL/hr, 7 mL/hr, 8 mL/hr, 9 mL/hr, 10 mL/hr, 15 mL/hr, 20 mL/hr, 25 mL/hr, 30 mL/hr, 40 mL/hr, 50 mL/hr, and so forth. The chamber is desirably rectangular but may also be circular, semi-circular, V-shaped, or any other appropriate shape.

Angle ($\theta$) is the angle between the horizontal axis with zero slope and a line having a slope along which the posts are distributed. (In this example, the angle provides a measure of the negative slope (tan ($\theta$)=$\Delta y/\Delta x$) of a row of posts.) In this example, it is understood that the posts may have a positive or negative slope, as each row of posts is arranged diagonally. Here, it is understood that diagonal may encompass any orientation that is not parallel or perpendicular to the chamber, e.g., an angle between 1 and 89 degrees, between 91 and 179 degrees, between 181 and 269 degrees, or between 271 and 359 degrees, clockwise or counter clockwise. Other exemplary angle ranges may be 1 to 10 degrees, 11 to 20 degrees, 21 to 30 degrees, 31 to 40 degrees, 41 to 50 degrees, 51 to 60 degrees, 61 to 70 degrees, 71 to 80 degrees, 81 to 90 degrees, 91 to 100 degrees, 101 to 110 degrees, 111 to 120 degrees, 121 to 130 degrees, 131 to 140 degrees, 141 to 150 degrees, 151 to 160 degrees, 161 to 170 degrees, or 171 to 180 degrees.

In general, multiple rows of posts are present in a chamber, and each row has the same slope or substantially the same slope as defined by angle ($\theta$). When cells 100 enter the chamber 105 of the microfluidics device, the cells flow through a plurality of paths (p) between the posts 115 in a lateral manner, towards a side of the chamber 105, until reaching a side of the chamber. For concentrating cells, the cells generally do not cross rows of posts, but rather, the cells typically travel along a particular path (p). The cells then exit the microfluidics chamber via output mechanism 122. In other embodiments, the posts may have a curvilinear component along the length of the chamber 105.

As used herein, the term "post" refers to a structure within the chamber having an associated in-plane dimension, an out-of-plane dimension, rotational angle, and shape. An in-plane dimension may refer to the length (l) and width (w) of the post, while the out-of-plane dimension may refer to the height (h) of the post. A tilting angle or a rotational angle ($\phi$) refers to the rotation of the post with respect to the chamber.

Shape refers to the 3-D characterization of the post, e.g., cylindrical, conical, pyramidal, cubic or cuboid, etc. In general, a post will be positioned such that its axis (out-of-plane dimension) is perpendicular to the surface to which it is affixed. In some embodiments, all posts within the chamber are of the same dimensions. In other embodiments, the dimensions of the posts vary as a function of space, such as depending on the position measured along the height (h) of the post. In general, the post may be of any shape, and is not limited to a particular geometric shape presented herein. The post shape may be arbitrary, as shown in FIG. 2R, represented by an axial length (l) and width (w), and a plurality of radii (r4-r12) associated with a curvature, positioned along the axial length, e.g., at a repeating constant interval or a repeating variable interval. Any number of different geometries may be described by the plurality of radii. Additionally, with reference to FIGS. 2R and 2S, one or more sides of the post may be in the shape of a straight line. Accordingly, the posts may have any suitable shape comprised of curves and/or straight lines.

In some embodiments, the posts are arranged at an interval (dx) along a line having a slope, wherein the interval is regularly spaced or fixed. For example, a post may be placed every 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 85 µm, 90 µm, 95 µm, 100 µm, and so forth, including any value in between these ranges depending upon the size of the cell to be concentrated.

In other embodiments, the posts are distributed along a line having a slope, such that the interval is not fixed but instead varies between any two successive posts. Any interval (dx) is permitted, provided that the interval is small enough to keep the cell from escaping path (p). For example, for a variable interval, a first post may be placed at a particular location, the second post may be placed 5 µm from the first post, a third post may be placed 4 um from the second post, and so forth. The interval can be selected based on the size of the cell.

In some embodiments, the interval can be selected to be sufficiently large to allow concentration of a particular type of cell, while allowing smaller cells to exit via output mechanism 120. For example, a blood sample may comprise a plurality of different cell types of relatively small size, including red blood cells, neutrophils (e.g., 12-14 µm in diameter), eosinophils (e.g., 12-17 µm in diameter), basophils (e.g., 14-16 µm in diameter), lymphocytes (e.g., 10-14 µm in diameter), and monocytes (e.g., 20 µm in diameter). Other types of cells in the human body are much larger, e.g., ranging from 40 to 100 µm in diameter or more. In such cases, the posts may be spaced to allow red and white blood cells to pass through, while concentrating larger cells (e.g., normal cells, tumor cells, etc.). The configuration of the posts (spacing) is determined based upon the type of cell being isolated. Different sheath-to-sample flow ratios can affect size-based sorting performance.

Each post has an associated length (l), width (w), also referred to as in-plane dimensions and a height (h), also referred to as an out of plane dimension (see also FIG. 2N). In some embodiments, the width of the post may be 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 85 µm, 90 µm, 95 µm, 100 µm, and so forth or any value in between. The length of the post may be 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 85 µm, 90 µm, 95 µm, 100 µm, and so forth or any value in between. In general, the posts may be of any shape (as viewed from the top-down orientation, and with respect to dimensions w and l), including but not limited to, circular, oval, square, rectangular, etc.

In the examples presented herein, the posts have an oval or rectangular shape. In some embodiments, the length of the post is 1.1 to 10 times greater than the width of the post; 1.1 to 5 times greater than the width of the post; 2 to 4 times greater than the width of the post; 3 to 4 times greater than the width of the post; or 2-3 times greater than the width of the post. In some embodiments, the length and width may have a ratio greater than or less than any of 20 to 1, 18 to 1, 16 to 1, 14 to 1, 12 to 1, 10 to 1, 9 to 1, 8 to 1, 7 to 1, 6 to 1, 5 to 1, 4 to 1, 3 to 1, 2 to 1, 1.1 to 1, or smaller or greater ratios.

In some embodiments, the cross section of the post may be defined by the intersection of the post with a plane that is parallel to a wall from which the post extends with height (h). The cross section may be symmetric along one or both of the length (l) and width (w) directions.

In still other embodiments, the length and the width of each post in the matrix are the same. In yet other embodiments, if the posts are circular, the radius of each post in the matrix is the same.

Additional features include the rotation angle ($\phi$) of the post, the height or the out of plane dimension of the post, spacing between the rows (dy), and offset of the rows (xo), which are described in additional detail in FIGS. 2N-2Q and throughout the application. As used herein, the term "rotational angle" refers to the degree of rotation of a post with regard to its position in the chamber. In some embodiments, the post has a length that is greater than its width. In this embodiment, a rotational angle of zero means that the length of the post is aligned with an axis perpendicular to a side of the chamber. To describe different rotational angles, the post may be rotated in a clockwise or counter clockwise direction. As an example, the posts in FIGS. 2M-Q are rotated about 35 degrees in a counter clockwise motion to arrive at the geometry of the posts shown in these figures.

Referring to FIG. 2N, each post has an associated height (h) or out of plane dimension, such that the posts are sufficiently tall to prevent the cells from escaping from path (p) by flowing in an upward path (e.g., over the top of the posts into a different path). For example, in some embodiments, the posts will span the height of the microfluidics chamber, such the posts are in contact with the floor of the chamber 160 and the ceiling of the chamber 150. In other embodiments, the height or out of plane dimension of the post may span a fraction of the total height of the microfluidics device. For example, the posts may have a height of 1 µm, 3 µm, 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 85 µm, 90 µm, 95 µm, 100 µm, and so forth, or any value in between.

Referring to FIG. 2O, each post has an associated rotation angle ($\phi$) or tilt, as shown from a top down view. In the present example, the rotation of the post is determined, starting with an orientation in which the length of the post is aligned with a first axis perpendicular to the side of the chamber and the width of the post is aligned with a second axis in line with the side of the chamber, by rotating the post in a counterclockwise direction, e.g., in this example, about 35 degrees counterclockwise, until reaching the desired rotation. Any rotation angle that facilitates flow of the cells through path (p) may be utilized, and all such rotation angles are contemplated herein. In some embodiments, the rotation angle is between 1 degree and 179 degrees, between 1 degree and 89 degrees, between 5 degrees and 85 degrees, between 10 degrees and 80 degrees, between 15 degrees and 75 degrees, between 20 degrees and 70 degrees, between 25 degrees and 65 degrees, between 30 degrees and 60 degrees, between 35 degrees and 55 degrees, between 40 degrees and 50 degrees, between 30 degrees and 40 degrees, between 32 degrees and 38 degrees, between 34 degrees and 36 degrees, or 35 degrees. In other embodiments, the rotation angle may be between 91 degrees and 179 degrees, between 95 degrees and 175 degrees, between 100 degrees and 170 degrees, between 105 degrees and 165 degrees, between 110 degrees and 160 degrees, between 115 degrees and 155 degrees, between 120 degrees and 150 degrees, between 125 degrees and 145 degrees, between 130 degrees and 140 degrees, or 135 degrees.

As indicated previously, the posts are distributed along a line having a negative slope. By orienting the cells along this line, the cells flowing through path (p) are directed laterally, towards a side of the chamber, while the solution that the cells are originally suspended in is able to flow in a manner (e.g., near horizontally or horizontally) to exit the microfluidics chamber via output mechanism 120.

Figure 2P:
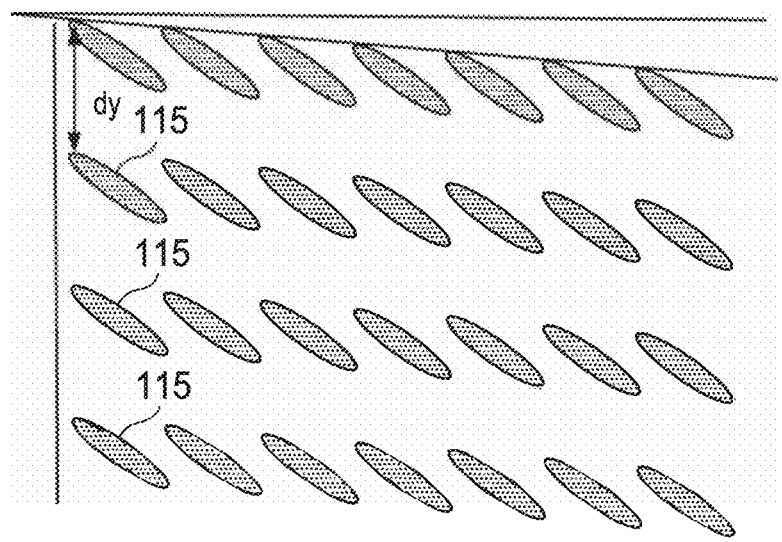

Referring to FIG. 2P, in still other embodiments, the rows of posts are spaced at an interval (dy). In some embodiments, the posts are arranged at an interval (dy) along a vertical line, wherein the interval is regularly spaced or fixed. For example, a post may be placed every 5 µm, 10 µm, 15 µm, 20 µm, 25 µm, 30 µm, 35 µm, 40 µm, 45 µm, 50 µm, 55 µm, 60 µm, 65 µm, 70 µm, 75 µm, 85 µm, 90 µm, 95 µm, 100 µm, and so forth, including any value in between, depending upon the size of the cell to be concentrated.

In other embodiments, the posts are distributed along a vertical line, such that the interval (dy) is not fixed but instead varies between any two successive rows of posts. For example, a first row of posts may be placed at a particular location, the second row of posts may be placed 5 µm from the first row of posts, a third row of posts may be placed 4 um from the second row of posts, and so forth, aligned with respect to a vertical line. The interval (dy) can be selected based on the size of the cell to be concentrated. Any interval (dy) is permitted, provided that the interval is sufficiently wide to allow flow of the solution through the chamber without requiring high pressures, which could damage the microfluidics device. In some embodiments, successive rows of posts may have a zero offset (xo).

Figure 2Q:
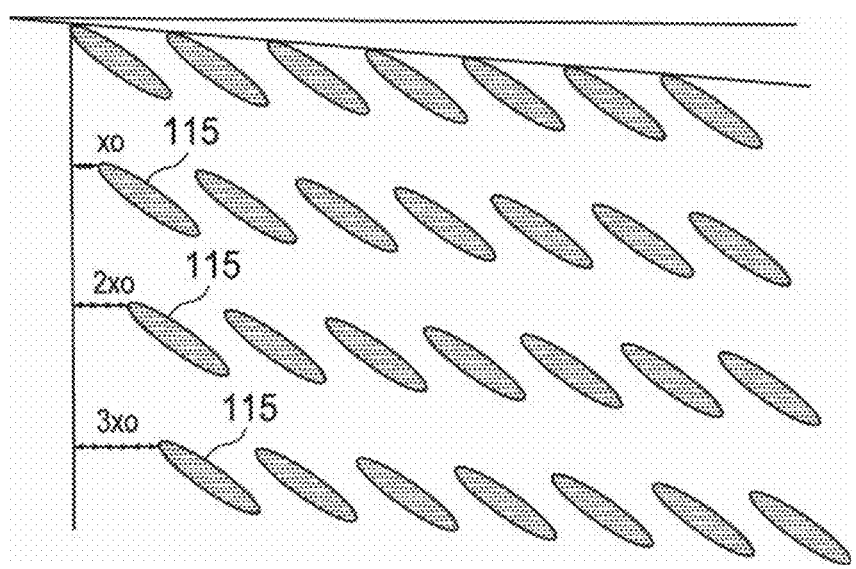
Figure 2R:
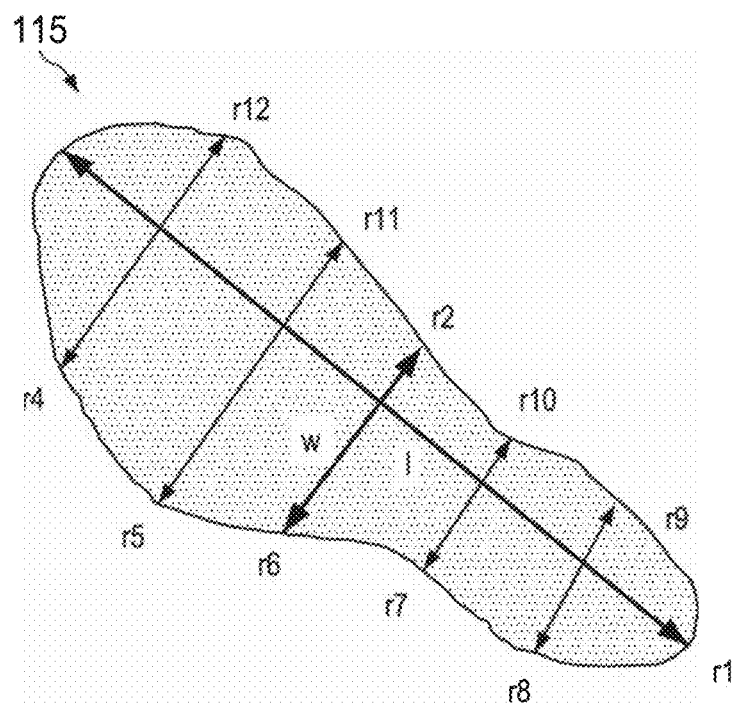
Figure 2S:
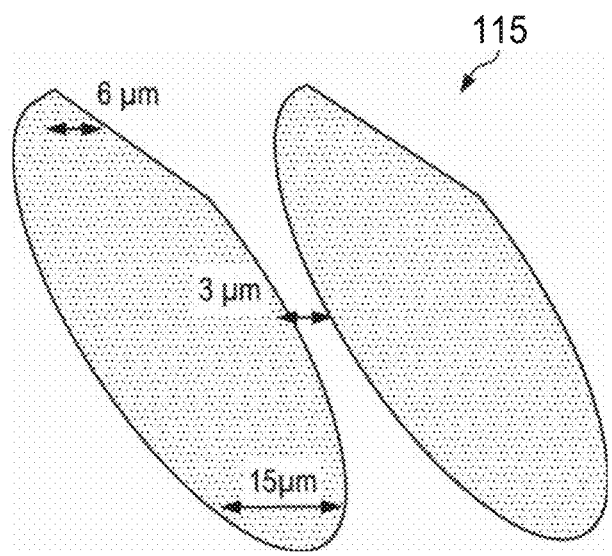

Referring to FIG. 2Q, successive rows of posts may have an offset (xo), relative to interval (dx). For example, a row (r) may be established at a particular location (e.g., using the Cartesian coordinate system x, y). The (r+1)th row may be displaced to the right by an amount (xo). The (r+2)th row may be displaced to the right by an amount (2xo). The (r+3)th row may be displaced to the right by an amount (3xo), and so forth up to the interval (dx). Offsets may occur in a fixed manner, such that each successive row is displaced in the same direction by a fixed amount. Alternatively, offsets may occur in a variable manner, such that each successive row is displaced in the same direction by a variable amount (up to the amount of (dx)). In other embodiments, offsets may be applied in an alternating direction, such that with regard to a row (r), the (r+1)th row has a fixed or variable offset in one direction, and the (r+2)th row has a fixed or variable offset in the opposite direction (e.g., one offset is to the right and the next offset is to the left).

The posts may be made out of any suitable material, including poly(dimethylsiloxane) (PDMS), glass, plastic, elastomers, silicon, etc. PDMS in general can be fabricated to have sub-micron resolution (e.g., below 0.1 µm features). In some embodiments, the chamber 105 and/or posts 115 may be made of PDMS. In other embodiments, the chamber may be fabricated of glass and/or silicon and/or plastic, and the posts may be fabricated using PDMS (e.g., the bottom of the chamber may be glass or silicon and the top of the chamber may be glass or plastic). Lithography, which is well known in the art, may be utilized to fabricate the chambers and posts as described herein. Materials having similar properties to PDMS may also be used to construct the microfluidic devices set forth herein.

Additionally, specific embodiments may comprise a number of additional features, including valves (e.g., between an input mechanism and the chamber, between the chamber and an output mechanism, between an output mechanism and another input mechanism or another chamber, etc.), pumps and mixers. In some embodiments, valves can be placed into PDMS during curation.

A variety of techniques can be employed to fabricate a microfluidics device. The microfluidics device may be formed from one or more of the following materials: poly (methylmethacrylate) (PMMA), polycarbonate, polystyrene, polyethylene, polyolefins, silicones (e.g., poly(dimethylsiloxane) PDMS), silicon, and combinations thereof. Other materials are well known in the art.

Methods for fabricating a chamber with posts and a microfluidics device using the materials referenced herein are also known in the art and include but are not limited to embossing, laser micromachining, milling, molding (e.g., thermoplastic injection molding, or compression molding), photolithography (e.g., stereolithography or x-ray photolithography), silicon micromachining, wet or dry chemical etching, etc.

Silicon fabrication techniques using photolithography followed by wet (KOH) or dry etching (reactive ion etching with fluorine or other reactive gas) can be employed for glass materials. For example, a glass master can be formed by conventional photolithography, which serves as a master template for molding techniques to generate a plastic or PDMS-based device.

A microfluidics device may be fabricated in one or more layers that are joined together, e.g., by adhesives, clamps, heat, solvents, etc. Alternatively, the microfluidics device may be fabricated as a single piece, e.g., using stereolithography or other three-dimensional fabrication techniques.

In some embodiments, due to the deformability of cells, a gap distance may be selected that is about 5 µm or less as compared to the size (e.g., a diameter) of the cell being concentrated. In other embodiments, the gap distance may be selected that is about 5 µm or greater as compared to the size (e.g., a diameter) of the cell being sorted. For rigid cells or microspheres having the same or similar diameter as a deformable cell, the gap distance may be different (e.g., larger for rigid cells) as compared to the gap distance for deformable cells of the same diameter.

Figure 2T:
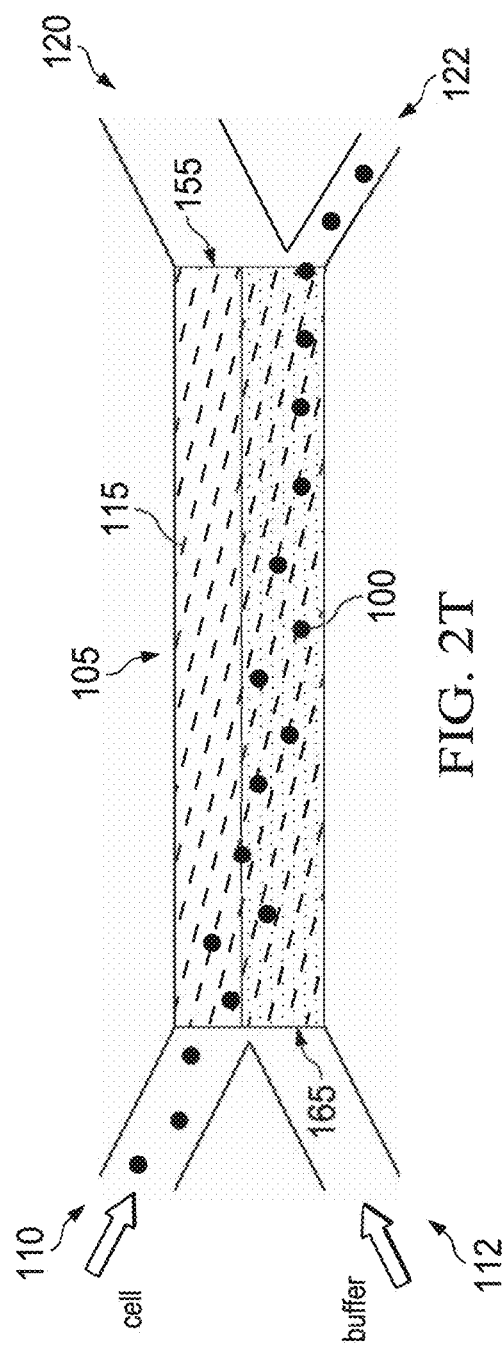
FIG. 2T illustrates an example microfluidics chamber for changing buffers according to some embodiments provided herein

FIG. 2T is an illustration of another example microfluidics cell concentrator. In this example, a first solution comprising cells 100 enters a chamber 105 at a first input mechanism 110. Cells are illustrated as circles. The cells pass through chamber 105, which comprises a matrix of posts 115, shown here as rectangular structures distributed along lines having a slope. As the cells pass in between the diagonally oriented rows of posts in the chamber, the cells are deflected laterally towards a side of the chamber. Similar to FIG. 2L, the chamber has a floor 160 (not shown) and an optional ceiling 150, which may be of the same material as the posts 115 or a different material.

In this example, a second input mechanism 112 is present in this system. A second solution (e.g., a buffer, which is different from the first solution entering the chamber through the first input mechanism 110) enters the chamber through the second input mechanism 112, for example buffer from buffer tube 577. In some embodiments, the first solution and the second solution do not substantially mix, and thus, the upper region of the chamber 155 comprises the first solution and has little if any of the second solution, while the lower region of the chamber 165 comprises the second solution and has little if any of the first solution. Thus, as the cells are deflected laterally and exit the chamber through output mechanism 122, the solution that exits the chamber via output mechanism 122 is in the second solution buffer.

Figure 2U:
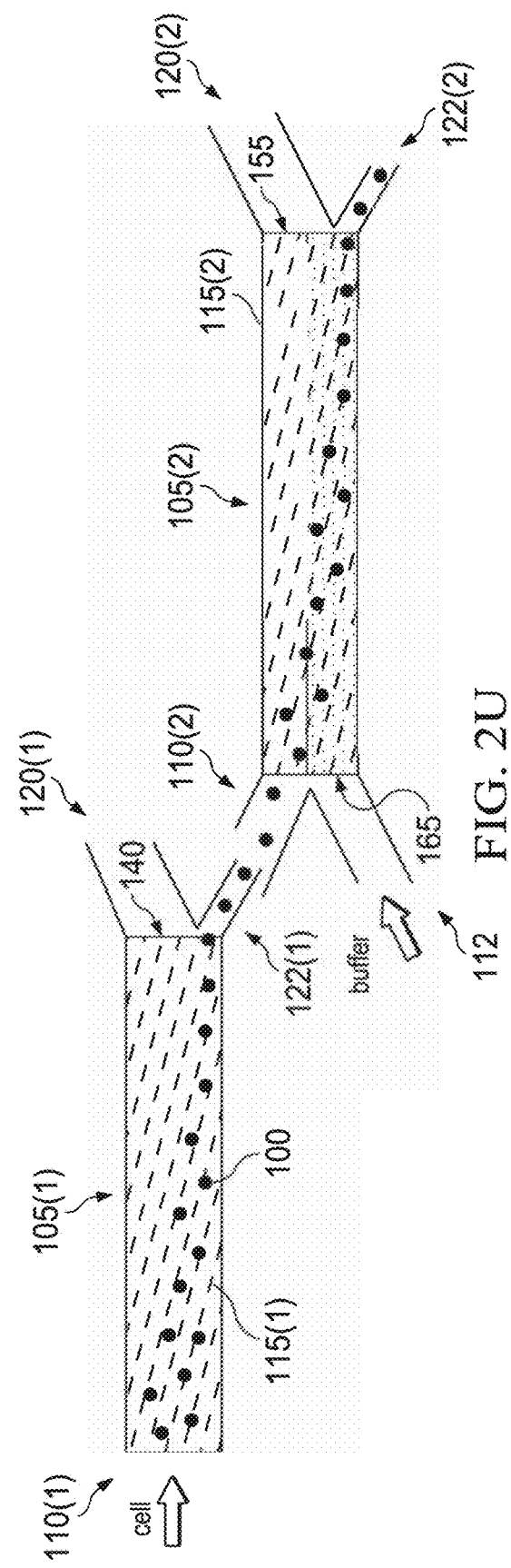
FIG. 2U illustrates an example microfluidics device having two separate chambers, one chamber for cell sorting and another chamber for buffer change according to some embodiments provided herein.

In some aspects, buffer changes may occur sequentially, in a cascade design, as shown in FIG. 2U. In this example, a first solution comprising cells 100 enters a first chamber 105(1) at a first input mechanism 110(1). Cells are illustrated as circles. The cells pass through chamber 105(1), which comprises a matrix of posts 115(1), shown here as rectangular structures distributed along lines having a slope. As the cells pass in between the diagonally oriented rows of posts in the chamber, the cells are deflected laterally. Similar to FIG. 2L, the chamber has a floor (160) (not shown) and an optional ceiling (150), which may be of the same material as the posts 115 or a different material. The cells (enriched) exit the chamber through output 122(1), which flows into input mechanism 110(2), where a second input mechanism 112 enters the system.

A second solution (e.g., a buffer), which is different from the first solution entering the chamber through the first input mechanism 110(1), enters the chamber through the second input mechanism (112). In some embodiments, the first solution and the second solution do not substantially mix, and thus, the upper region of the chamber (155) comprises the first solution and has little if any of the second solution, while the lower region of the chamber (165) comprises the second solution and has little if any of the first solution. The cells (enriched and in the buffer from input mechanism 112) exit chamber 105(2) through output mechanism 122(2).

In other aspects, buffer changes may occur in parallel. For example, the flow path may be divided so that the sample flows into multiple chambers, wherein each chamber includes an input mechanism for a buffer. With this configuration, the same buffer may be supplied to each of the parallel chambers, such that the cells are concentrated into the same buffer. Alternatively, each of the parallel chambers may be supplied with a different buffer, such that the cells are concentrated into different buffers, e.g., for different downstream assays.

In general, the input mechanism can be driven by a syringe pump or by manual depression of a syringe. In some aspects, for multiple inputs, one or more syringe pumps can be used to drive each input in an automated manner. In other aspects, for multiple inputs, manual depression of one or more syringes can be used to drive each input manually.

In any embodiment, an electroporation apparatus capable of providing different electroporation effects is described herein. For example, as illustrated in FIG. 2V, an electroporation device 600 having three electrodes 640(1), 640(2), 640(3) (e.g., each can be a mesh or plate electrodes) is provided. The electroporation device 600 includes two paths for cells and cargo to travel, a first path between electrode 640(1) and electrode 640(2) and a second path between electrode 640(2) and electrode 640(3) where the arrows indicate flow of cells. The DCs can enter an electroporation chamber at inlet 620 and exit via outlet 630. Although not shown, it is contemplated herein that more than one outlet may be present, for example, each outlet can collect different types of cells. Different electrode gap lengths (L1, L2, L3, L4) are present in the electroporation device 600. The different electrode gap lengths and different paths result in a different capacitance; therefore, different electric field strength and electroporation effect can be achieved for the cells traveling in each path. For example, L2 can be greater than L4, and in such instance, a capacitance (C1) in the first path can be greater than a capacitance (C2) in the second path (C1>C2). In any embodiment, DCs may be pre-sorted and/or selected, for example, using the microfluidics devices described above, to enter the first path or the second path.

Figure 2W:
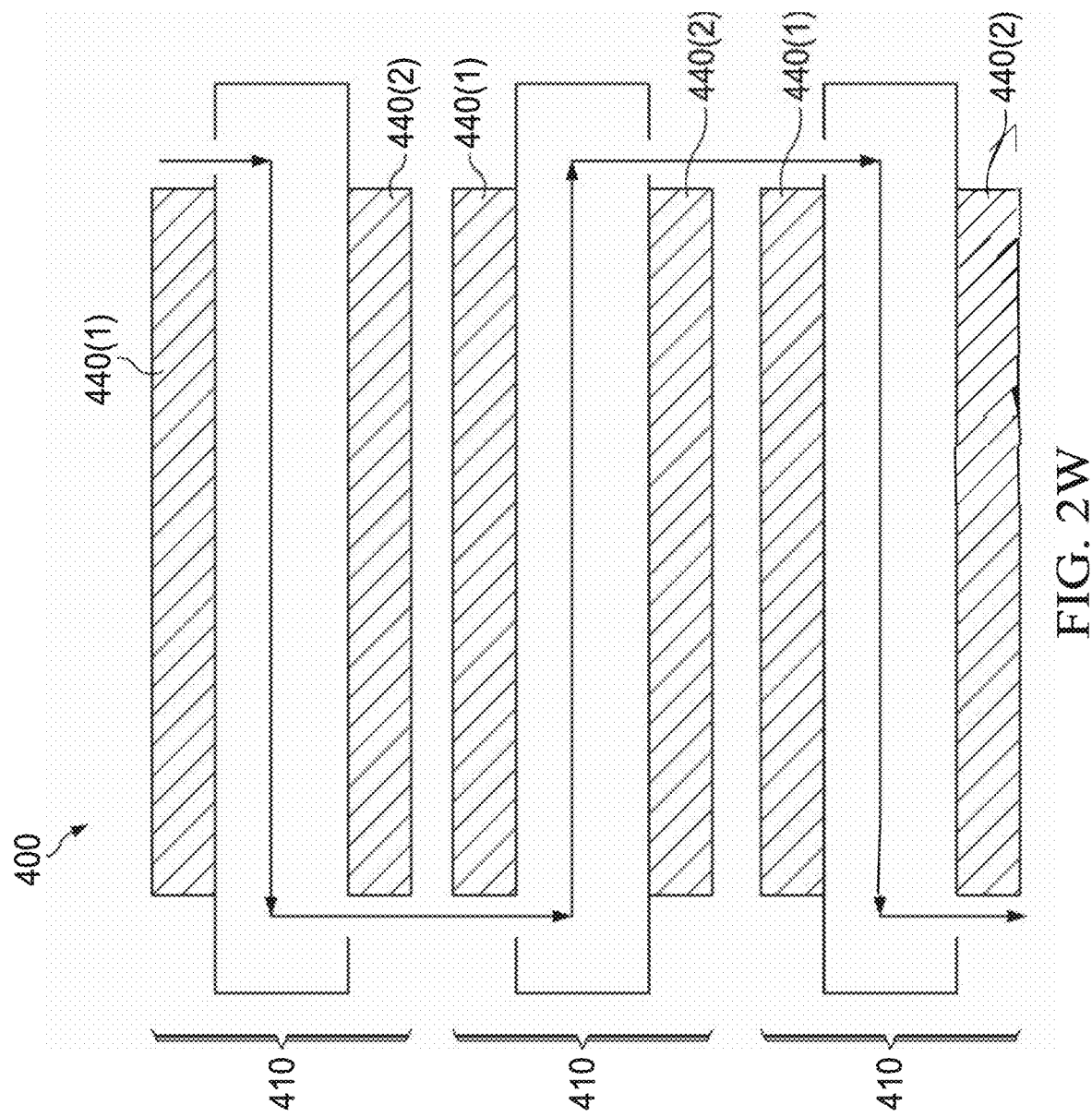

It is also contemplated herein that the electroporation devices described herein can be present as cartridges, which may be in fluid communication with one another (e.g., connected, stacked), to provide a path of desired length and geometry. For example, as illustrated in FIG. 2W, cartridges 410 each include an electroporation chamber including an upper electrode 440(1) and a lower electrode 440(2) (e.g., each can be a mesh or a plate electrode), wherein the cartridges may be stacked in series with the arrows showing flow of cells through the cartridges. For example, an outlet of topmost cartridge 410 is in fluid communication with an inlet of middle cartridge 410 and an outlet of middle cartridge 410 is in fluid communication with an inlet of lowermost cartridge 410.

The electroporation apparatuses described herein have a number of advantages over mesh-based electroporation devices, such as the configuration shown in FIG. 1B. First, the traveling distance through the electroporation chamber, as measured from first input to the first output of the electroporation chamber, may be increased without leading to a corresponding increase in the electric field. Thus, cells are exposed to a uniform electric field for a greater length of time than in a strictly linear flow path, which leads to improved electroporation efficiency, without a corresponding decrease in viability.

Although the electroporation chamber width (w) between the upper mesh electrode and the lower mesh electrode could be increased in FIG. 1B to provide a longer traveling distance, a larger electroporation chamber width would have a larger impedance, and a higher voltage would need to be applied to generate a suitable electric field. Additionally, the larger voltage would likely have an adverse impact on cellular viability. Further, for parallel plate electrode configurations, as in FIG. 1A, the electric field distribution would not be uniform.

Thus, according to embodiments, the electroporation apparatuses described herein can have a shorter electrode pair due to the offset input output design, which extends the electroporation chamber length without increasing the electrode pair distance.

FIG. 3 provides a table illustrating differences between an electroporation device as described herein and electroporation devices in the prior art. Such differences include, but are not limited to: (1) presence of the input output offset distance, (2) use of a low conductance low osmolarity electroporation media, instead of commercially available electroporation media such as BTX and RPMI, (3) exponentially discharging waveforms, applied in a series of electrical pulses, and (4) a stepping fluid flow scheme.

Figure 5:
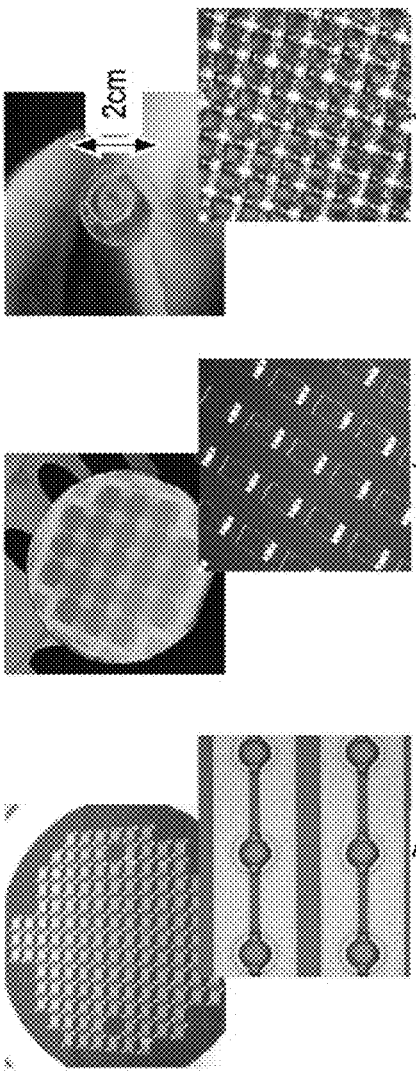
FIG. 5 shows various examples of micromeshes formed of different materials suitable for use with a chamber offset electroporation device, according to some embodiments provided herein.

While the example in FIGS. 2A-2C utilizes stainless steel micromesh electrodes, the electrodes are not limited to any particular material and may be formed of any suitable material. For example and as shown in FIG. 5, suitable material include silicon, polyimide, and micromesh. Silicon and polyimide may be used to form suitable electrodes, however, such materials are typically processed in clean room facilities using microfabrication protocols known in the art. In contrast, stainless steel electrodes, e.g., stainless steel micromesh electrodes, are easy to set up and do not require specialized facilities, such as clean rooms.

For using electrodes having a porosity, it is understood that any suitable material may be used provided that the electrode has pores allowing passage of cells (e.g., the pores are larger than the cells), and that the pores are compatible with electrode patterning around the pore opening.

Methods of Preparing Antigen-Loaded DCs and Electroporation Parameters

Methods of preparing antigen-loaded DCs are provided herein, for example, with the electroporation apparatuses as described above. In various aspects, the antigen-loaded DCs can be used for cancer treatment, for example, in a cancer vaccination. In any embodiment, the DCs can be derived from or isolated from a subject with techniques known by those of ordinary skill in the art. Suitable methods for isolating and culturing DCs are described, for example, in US 2004/0241147. Similarly, tumor cells comprising antigens can be isolated from the subject with techniques known by those of ordinary skill in the art. The tumor cells can be selected from the group consisting of melanoma cancer cells, breast cancer cells, prostate cancer cells, pancreatic cancer cells, ovarian cancer cells, and colon cancer cells. In any embodiment, immunogenic cell death of the tumor cells can be induced, for example, via ultraviolet (UV) radiation or chemically, to form a tumor cell lysate (TCL) containing antigens. The antigens may or may not be separated from the TCL. Where it is regarded as desirable to purify antigens from the TCL before exposing DCs to the antigens, the purification can be worked by any of a variety of suitable methods known in the art (e.g., column chromatography, isoelectric focusing, gel electrophoresis, immune affinity capture, etc). Optionally, the TCL and/or antigens can be incubated with the DCs for a specified period of time prior to electroporation.

The methods can include flowing the DCs and the TCL and/or antigens into an electroporation chamber. The electroporation chamber includes an upper electrode as described herein, a lower electrode as described herein, and a path defined between the upper electrode and the lower electrode for the DCs and antigens to flow as described herein. The upper electrode can have a first porosity as described herein and the lower electrode can have a second porosity as described herein. Additionally, the upper electrode can be bounded by a first material as described herein. The first material can include a first input as described herein allowing passage of DCs into the electroporation chamber. The lower electrode can be bounded by a second material. The second material can include a first output as described herein allowing passage of electroporated cells including antigen-loaded DCs from the electroporation chamber. The first input and the first output are separated by an offset distance as described herein. The DCs can be suspended in an electroporation medium. Optionally, the upper electrode may further include a second input as described herein and/or the lower electrode may further include a second output as described herein.

Figure 4:
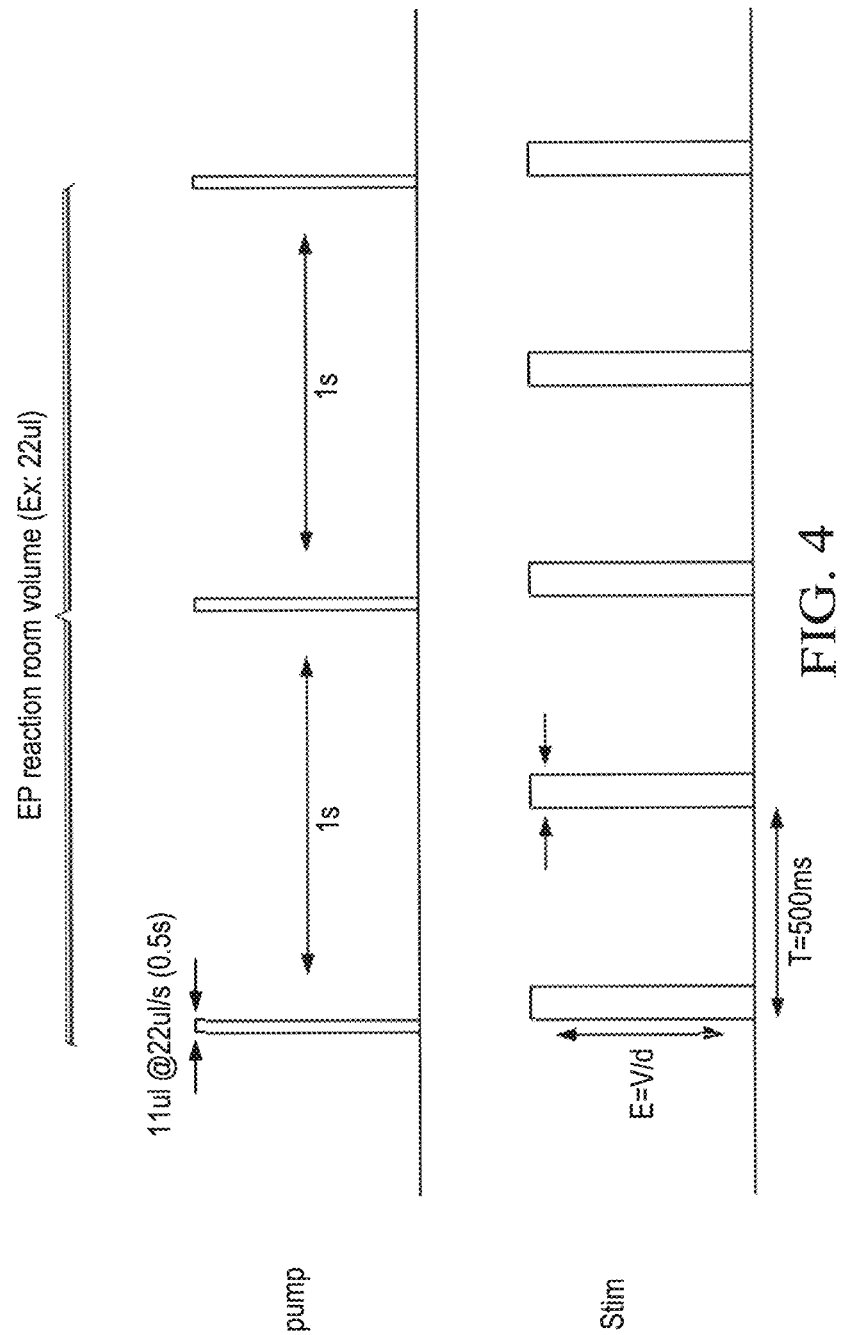
FIG. 4 shows examples of fluid flow waveforms (pump) and electric waveforms (stim) that may be applied to cells flowing through the chamber offset electroporation device, according to some embodiments provided herein.

In any embodiment, flowing of the DCs and TCL and/or antigens may be performed in a stepwise manner. For example, a fluid volume of about half a total volume of the electroporation chamber can be pumped into the electroporation chamber at a designated interval of time. FIG. 4 shows an example series of electrical pulses (stim) and an example stepping fluid flow scheme (pump). For the stepping fluid flow scheme, the chamber volume is approximately 22 µL. Every second, 11 µL is pumped into the electroporation chamber, displacing half the volume. This may be repeated as long as needed to process a desired amount of cells.

Any suitable interval of time may be used along with any suitable volume for the stepping fluid flow scheme. For example, the interval of time may range from about 0.1 seconds to about 10 seconds, from about 0.5 seconds to about 5 seconds, from about 1 second to about 2 seconds, or any period of time in between, or may include longer intervals. In some aspects, the amount of fluid pumped into the electroporation chamber as a function of time may be three-fourths the volume of the input chamber, one-half the volume of the electroporation chamber, one-fourth the volume of the electroporation chamber, one-eighth the volume of the electroporation chamber, or smaller.

In any embodiment, at least a portion or substantially all of the DCs are exposed to a uniform or a substantially uniform electrical field within the electroporation chamber. Multiple electrical pulses can be applied to the DCs within the electroporation chamber, wherein each electrical pulse is the same or different. In some embodiments, a direct current (DC) electrical pulse is applied. Additionally or alternatively, an alternating current (AC) electrical pulse is applied. In any embodiment, each pulse can have a form of an exponentially discharging waveform or a square waveform. In any embodiments, the multiple electrical pulses can include both an exponentially discharging waveform or a square waveform.

For the series of electrical pulses, every 100 ms to 5000 ms (e.g., every 100 ms, every 250 ms, every 500 ms, every 1000 ms, every 2000 ms, every 3000 ms, etc), a voltage can be applied to the electrodes to generate an electric field of a given strength. This may be repeated as long as needed to process a desired amount of DCs. Accordingly, while aspects may be referred to as continuous flow, it is understood that continuous flow includes a stepping fluid flow scheme, in which fluid is continually pumped into the electroporation chamber according to a defined time interval.

Any suitable interval of time may be used along with any suitable duration of electrical pulse for cells in the electroporation chamber. For example, the interval of time between pulses may range from about 0.1 seconds to about 5 seconds, from about 0.2 seconds to about 1 second, from about 0.4 seconds to about 0.6 seconds, or any period of time in between, and may include longer intervals. In some aspects, the duration of the electrical pulse may range from about 10 ms to about 250 ms, from about 50 ms to about 150 ms, from about 75 ms to about 125 ms, 0.1 seconds to about 4 seconds, or any range in between.

In further contemplated aspects, the medium or electroporation buffer in which the cells are transfected is a low conductivity and low osmolarity medium, optionally containing one or more nutrients. Therefore, suitable media include but are not limited to: Cw100 (0.11 S/m, 0.12 osm/l) or Cw240. Commercially available electroporation media may be utilized, but was shown to be suboptimal. Such commercially available media include: RPMI (1.375/m, 0.28 osm/l) and BTX (8 mS/m, 0.27 osm/l). Suitable conductances may range from about 0.05 mS/m to about 0.2 S/m. Suitable osmolarities may range from about 0.05 osm/l to about 0.2 osm/l. The media are generally electrically conductive media and may also be sterile.

TABLE 1

Composition of electroporation media

|  | $KH_2PO_4$ | $Na_2HPO_4$ | $MgSO_4$—$7H_2O$ | Sucrose | HEPES |
|---|---|---|---|---|---|
| Cw240 | 2 mM | 5 mM | 1 mM | 200 mM | 15 mM |
| Cw100 | 2 mM | 0 mM | 1 mM | 99 mM | 20 mM |

With respect to suitable capacitances, it is contemplated that the capacitance may range from about 1 µF to about 150 µF. In some embodiments, the capacitance may range from about 1-100 µF, from about 5 to about 75 µF, from about 5 to about 50 µF, from about 10 to about 40 µF, or from about 10 to about 30 µF, or from about 10 to about 25 µF. In other embodiments, the capacitance is about 10 µF.

In some embodiments, multiple electrical pulses, along with a corresponding short time constant may be utilized. In some aspects, a time constant of less than 30 msec, less than 20 msec, less than 10 msec, or less than 5 msec may be used. In other aspects, a time constant may range from about 0.5 to 30 msec, from about 1 to 20 msec, and from about 5 to 15 msec; or about 10 msec to 30 msec.

In some aspects, the electrical field strength for electroporation is between about 0.3-3 kV/cm. Lower electrical field strengths (e.g., about 0.5-1 kV/cm) were found to be suitable for EC-7 cells, while higher electrical field strengths (e.g., about 1-3 kV/cm) were found to be suitable for hank cells. In general, electrical field strengths for electroporation ranging from about 0.1 to about 5 kV/cm are contemplated herein. The voltage may be selected to generate suitable electrical field strengths.

In general, the impedance (Rp) may range from about 200Ω up to infinity, or in other cases, from about 200Ω up to about 1 k.

The concentration of antigens added to the electroporation reaction, e.g., the material to be transported into the DCs, can have a concentration of about 1 µg/ml to about 100 µg/ml, or about 50 µg/ml.

With respect to suitable pulse numbers and pulse-to-pulse intervals, at least two, three, and four pulses may provide more desirable results than a single pulse or of five or more pulses. Therefore, it is contemplated that pulses may range between 2-4 pulses. Most typically, the pulses are separated from subsequent pulses by a relatively short interval, typically between 0.5 second and 15 seconds, though in some cases even longer intervals may be used.

In some aspects, up to 7.33 uL/s@$4\times10^7$ cells/ml (13.2 mL ($5.28\times10^8$ cells) in 30 mins can be achieved in a single chamber device. To reach $20\times10^9$ cells in 30 mins, the cell density may be increased four-fold and/or parallel processing may be performed using multiple electroporation chambers.

In embodiment, the methods described herein may further include a first cell sorting step and/or a second cell sorting step, for example, using the microfluidics devices as described herein. The first cell sorting step can sort the DCs prior to introduction into the electroporation chamber by applying pressure to cause a first solution comprising the DCs to flow through a microfluidics chamber as described herein comprising a plurality of rows of posts as described herein and deflecting the DCs to a side of the chamber by the rows of posts to deplete cells from the solution exiting a first output mechanism as described herein and enrich cells in the solution exiting a second output mechanism as described herein. The DCs exiting the second output mechanism can be introduced into the electroporation chamber with the cargo. The second cell sorting step can sort the electroporated cells after exiting the electroporation chamber by applying pressure to cause a fourth solution comprising the electroporated cells to flow through a microfluidics chamber as described herein comprising a plurality of rows of posts as described herein and deflecting the electroporated cells to a side of the chamber by the rows of posts to deplete electroporated cells from the solution exiting a third output mechanism as described herein and enrich electroporated cells in the solution exiting a fourth output mechanism as described herein.

The techniques and methods provided herein may be integrated into a variety of devices or platforms as part of a workflow. For example, an electroporation apparatus as described herein can be incorporated into an automated device, for example, in cartridge form, wherein electroporation can be performed along with one or more other automated processes on cells. For example, automated electroporation can be performed along with automated cell culturing and harvesting as described in U.S. Patent Publication No. 2017/0037357, which is incorporated by reference in its entirety.

The methods may further include culturing or proliferating or growing the antigen-loaded DCs by techniques known in the art to produce cultured antigen-loaded DCs. The cultured antigen-loaded DCs can be incorporated into a vaccination, for example, for cancer treatment.

In other aspects, antigen-loaded DCs prepared according the above-described methods are provided herein.

In other aspects, methods of treating cancer in a subject in need thereof are provided. The method includes administering antigen-loaded DCs prepared according to the above-described methods to the subject. The method can further include administering anti-PD-1 therapy to the subject.

EXAMPLES

Example 1. Transfection of DCs with Tumor Antigens

To prepare antigen-loaded DCs for immunotherapy, isolate and enrichDCs from a patient suffering from cancer, for example using a blood dentric cell isolation and enrichment kits known in the art.

Isolate tumor cells from the patient suffering from cancer. The tumor cells are adjusted to $4\times10^6$ cells/ml in R10 medium, 1.5 ml per well plated in 6-well plates (Corning) and treated with 300 mJ/cm2 UV irradiation using a Stratalinker UV Crosslinker 1800 (Stratagene). Cells are cultured for 16-24 h at 37° C. in 5% CO2, subjected to 3 freeze (−80° C.)/thaw (37° C.) cycles of minimum 30 min each and passed through a 40 µm cell strainer before addition to DCs at a ratio of 1 DC to 2 tumor cells. Tumor cell lysate (TCL) is twice washed with R10 and centrifuged at full-speed to remove soluble components and obtain washed TCL comprising antigens.

Bring the DCs derived from the patient and the washed TCL comprising antigens into contact. Optionally incubate together for a period of time.

Transfect the DCs by electroporating the DCs with TCL using an IOCO electroporation device as shown in FIGS. 2A-2D to create antigen-loaded DCs.

Culture and purify the antigen-loaded DCs and administer the antigen-loaded DCs to the patient as an immunotherapy treatment.

In some embodiments, the numbers expressing quantities of ingredients, properties such as concentration, reaction conditions, and so forth, used to describe and claim certain embodiments are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments are approximations, the numerical values set forth in the specific examples are reported as precisely as practicable. The numerical values presented in some embodiments may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should also be apparent to those skilled in the art that many more modifications besides those already described herein are possible without departing from the inventive concepts herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of preparing antigen-loaded dendritic cells (DCs) for the treatment of cancer in a subject, the method comprising:
    electroporating DCs in the presence of antigens to form the antigen-loaded DCs, wherein the DCs are syngeneic to the subject, and wherein the electroporating comprises:
        flowing an electroporation medium comprising the DCs and the antigens into an electroporation chamber,
        wherein the electroporation medium has a conductance of 0.05 mS/m to about 0.2 S/m and an osmolarity of about 0.05 osm/L to about 0.2 osm/L,
        wherein the electroporation chamber comprises an upper electrode, a lower electrode, and a path defined between the upper electrode and the lower electrode for the electroporation medium to flow,
        wherein the upper electrode is bounded by a first material comprising a first input allowing the DCs and the antigens to flow into the electroporation chamber,
        wherein the lower electrode is bounded by a second material comprising a first output allowing the flowing of the antigen-loaded DCs from the electroporation chamber, and
        wherein the first input and the first output are separated by an offset distance; and
    pulsing an electric current between the upper and the lower electrodes to create an electric field while the DCs and the antigens flow across the offset distance toward the first output of the electroporation chamber,
    wherein the DCs and the antigens flow through the electroporation chamber in a direction perpendicular to a direction of the electric field.

2. The method of claim 1, further comprising preparing the antigens by inducing immunogenic cell death of tumor cells isolated from the subject by UV irradiation to form a tumor cell lysate containing the antigens.

3. The method of claim 2, further comprising incubating the DCs with the antigens prior to the electroporation.

4. The method of claim 3, wherein the flowing is performed in a stepwise manner, wherein a fluid volume of the electroporation medium of about half a total volume of the electroporation chamber is pumped into the electroporation chamber at a designated interval of time.

5. The method of claim 4, wherein the offset distance is 2 mm or greater.

6. The method of claim 5, wherein a width of the electroporation chamber is about 0.01 mm to about 2 mm.

7. The method of claim 6, wherein the DCs within the electroporation chamber flow laterally in the path along the length of the electroporation chamber.

8. The method of claim 6, wherein the DCs are exposed to a uniform or a substantially uniform electrical field within the electroporation chamber.

9. The method of claim 6, further comprising applying multiple electrical pulses to the DCs within the electroporation chamber.

10. The method of claim 9, wherein the multiple electrical pulses are each applied at a field strength of about 0.3 kV/cm to about 3 kV/cm.

11. The method of claim 10, wherein the multiple electrical pulses are each applied at the field strength of about 1 kV/cm to about 1.3 kV/cm.

12. The method of claim 10, wherein the multiple electrical pulses are each applied at the field strength of about 0.3 kV/cm to about 1 kV/cm.

13. The method of claim 10, wherein one or more of the following occurs:
    (a) each electrical pulse has a form of an exponentially discharging waveform or a square waveform;
    (b) a time interval between each electrical pulse is about 0.5 seconds to about 15 seconds;
    (c) a duration of each electrical pulse is about 0.1 seconds to about 5 seconds;

(d) a time constant is from about 10 msec to about 30 msec;
(e) the electrical pulses are delivered from a capacitor having a capacitance from about 5 g to about 75 g; and
(f) the field strength is applied at a voltage of about 40V.

14. The method of claim 13, wherein the tumor cells are selected from the group consisting of melanoma cancer cells, breast cancer cells, prostate cancer cells, pancreatic cancer cells, ovarian cancer cells, and colon cancer cells.

15. The method of claim 14, further comprising culturing the antigen-loaded DCs.

16. The method of claim 6, wherein the upper electrode has a first porosity which allows the flowing of the DCs and the antigens from the first input through the upper electrode into the electroporation chamber and/or the lower electrode has a second porosity which allows the flowing of the antigen-loaded DCs through the lower electrode and the first output from the electroporation chamber.

17. The method of claim 16, wherein the upper electrode further comprises a second input to allow the flowing of the DCs and the antigens into the electroporation chamber, and/or the lower electrode further comprises a second output to allow the flowing of the antigen-loaded DCs from the electroporation chamber.

18. The method of claim 17, wherein the path is linear.

19. The method of claim 1, wherein the DCs and the antigens flow through the first input in a first direction, the DCs and the antigens flow laterally through the electroporation chamber in a direction perpendicular to the first direction, and the antigen-loaded DCs flow through the first output in a second direction parallel to the first direction.

20. A method of treating a tumor in a human subject in need thereof, the method comprising:
electroporating DCs in the presence of a tumor cell lysate containing antigens to form antigen-loaded DCs, wherein the DCs are syngeneic to the human subject and the antigens and the tumor cell lysate are from the tumor of the human subject, wherein the electroporating comprises:
flowing an electroporation medium comprising the DCs and the tumor cell lysate containing the antigens into an electroporation chamber,
wherein the electroporation medium has a conductance of 0.05 mS/m to about 0.2 S/m and an osmolarity of about 0.05 osm/L to about 0.2 osm/L,
wherein the electroporation chamber comprises an upper electrode, a lower electrode, and a lateral path defined between the upper electrode and the lower electrode for the electroporation medium, the DCs, and the tumor cell lysate containing the antigens to flow,
wherein the upper electrode is bounded by a first material comprising a first input allowing the DCs and the tumor cell lysate containing the antigens to flow into the electroporation chamber,
wherein the lower electrode is bounded by a second material comprising a first output allowing the flowing of the antigen-loaded DCs from the electroporation chamber, and
wherein the first input and the first output are separated by an offset distance; and
pulsing an electric current between the upper and the lower electrodes to create an electric field while the DCs and the tumor cell lysate containing the antigens flow across the offset distance toward the first output of the electroporation chamber to form the antigen-loaded DCs,
wherein the DCs and the tumor cell lysate containing the antigens flow through the electroporation chamber along the lateral path in a direction perpendicular to a direction of the electric field; and
administering the antigen-loaded DCs to the human subject, wherein the antigen-loaded DCs mediate the treatment of the cancer.

* * * * *